United States Patent
Kreyenschmidt et al.

(10) Patent No.: US 10,138,307 B2
(45) Date of Patent: **\*Nov. 27, 2018**

(54) ANTIMICROBIAL POLYMER

(71) Applicant: Fachhochschule Münster, Steinfurt (DE)

(72) Inventors: Martin Kreyenschmidt, Lohne (DE); Reinhard Lorenz, Steinfurt (DE); Björn Fischer, Saerbeck (DE); Judith Kreyenschmidt, Rheinbach (DE); Florian Brodkorb, Steinfurt (DE); Katrin Kalbfleisch, Havixbeck (DE); Tobias Blang, Münster (DE); Adrian Geschwentner, Steinfurt (DE)

(73) Assignee: Fachhochschule Münster, Steinfurt (DE)

( * ) Notice: Subject to any disclaimer, the term of this patent is extended or adjusted under 35 U.S.C. 154(b) by 102 days.

This patent is subject to a terminal disclaimer.

(21) Appl. No.: 14/764,610

(22) PCT Filed: Jan. 31, 2014

(86) PCT No.: PCT/EP2014/051955
§ 371 (c)(1),
(2) Date: Jul. 30, 2015

(87) PCT Pub. No.: WO2014/118339
PCT Pub. Date: Aug. 7, 2014

(65) Prior Publication Data
US 2015/0368380 A1    Dec. 24, 2015

(30) Foreign Application Priority Data

Jan. 31, 2013  (EP) .................................... 13000471
Mar. 28, 2013  (EP) .................................... 13001644

(51) Int. Cl.

| | | |
|---|---|---|
| *C08F 26/02* | (2006.01) | |
| *A01N 33/04* | (2006.01) | |
| *C08F 12/28* | (2006.01) | |
| *C08F 112/14* | (2006.01) | |
| *C08F 212/14* | (2006.01) | |
| *A01N 37/34* | (2006.01) | |
| *A01N 37/44* | (2006.01) | |
| *A01N 43/40* | (2006.01) | |
| *C08F 26/06* | (2006.01) | |

(52) U.S. Cl.
CPC .............. *C08F 26/02* (2013.01); *A01N 33/04* (2013.01); *A01N 37/34* (2013.01); *A01N 37/44* (2013.01); *A01N 43/40* (2013.01); *C08F 12/28* (2013.01); *C08F 26/06* (2013.01); *C08F 112/14* (2013.01); *C08F 212/14* (2013.01); *Y10T 156/10* (2015.01)

(58) Field of Classification Search
CPC ........... C08F 26/02; C08F 12/28; A01N 33/04
See application file for complete search history.

(56) References Cited

U.S. PATENT DOCUMENTS

| | | |
|---|---|---|
| 4,447,580 A | 5/1984 | Ai et al. |
| 4,482,680 A | 11/1984 | Sheldon et al. |
| 5,520,910 A | 5/1996 | Hashimoto et al. |
| 5,536,861 A | 7/1996 | Robertson |
| 2001/0007694 A1 | 7/2001 | Ottersbach et al. |
| 2006/0228966 A1 | 10/2006 | Gleason et al. |
| 2006/0234059 A1 | 10/2006 | Cella et al. |
| 2011/0015615 A1 | 1/2011 | Cichos et al. |
| 2011/0313383 A1 | 12/2011 | Hofstetter et al. |

FOREIGN PATENT DOCUMENTS

| | | |
|---|---|---|
| DE | 10 2006 006 675 A1 | 9/2007 |
| DE | 10 2008 013 143 A1 | 9/2009 |
| JP | S58-25313 A | 2/1983 |
| JP | H05-285469 A | 11/1993 |
| JP | 2000-239281 A | 9/2000 |
| WO | 00/69938 A1 | 11/2000 |
| WO | 01/62810 A1 | 8/2001 |
| WO | 01/87998 A2 | 11/2001 |

OTHER PUBLICATIONS

Martin, T. P., et al. "Initiated chemical vapor deposition of antimicrobial polymer coatings." Biomaterials 28.6 (2007): 909-915.*
Gelman, Michael A., et al. "Biocidal activity of polystyrenes that are cationic by virtue of protonation." Organic Letters 6.4 (2004): 557-560.*
Muñoz-Bonilla, Alexandra, and Marta Fernández-García. "Polymeric materials with antimicrobial activity." Progress in Polymer Science 37.2 (2012): 281-339.*
Jiang, Shan, et al. "Study on antibacterial behavior of insoluble quaternary ammonium." Journal of Applied Polymer Science 99.5 (2006): 2389-2394.*
Dohlen et al.: "Potential of the polymer poly-[2-(tert-butylamino)methylstyrene] as antimicrobial packaging material for meat products", Journal of Applied Microbiology, 2016, vol. 121, pp. 1059-1070.
Braun et al.: "Antimicrobial Activity of Intrinsic Antimicrobial Polymers Based on Poly((tert-butyl-amino)-methyl-styrene) Against Selected Pathogenic and Spoilage Microorganisms Relevant in Meat Processing Facilities", 2017, J Antimicrob Agents, vol. 3, issue 1, 1000136, pp. 1-9.

* cited by examiner

*Primary Examiner* — Bethany P Barham
*Assistant Examiner* — Peter Anthopolos
(74) *Attorney, Agent, or Firm* — Jason D. Voight

(57) ABSTRACT

The invention is directed to an antimicrobial polymer that can preferably be processed thermoplastically, a method for the preparation of said antimicrobial polymer and its use in antimicrobial treatment. The invention is further directed to polymer blends containing antimicrobial polymers and the use of special monomers in the preparation of antimicrobial polymers that can be processed thermoplastically.

20 Claims, No Drawings

ANTIMICROBIAL POLYMER

This is the national stage of International Application PCT/EP2014/051955, filed Jan. 31, 2014.

The invention is directed to an antimicrobial polymer that can preferably be processed thermoplastically, a method for the preparation of said antimicrobial polymer and its use in antimicrobial treatment. The invention is further directed to polymer blends containing antimicrobial polymers and the use of special monomers in the preparation of antimicrobial polymers that can be processed thermoplastically.

It has long been known to impart antimicrobial properties to polymers through the addition of certain additives such as silver, zinc and copper. The antimicrobial effect of silver in laboratory conditions has often been proven (Carr et al. 1973, Russel & Hugo 1994, Hipler et al. 2006, Kampmann et al. 2008b). The principle according to which the effect is obtained is based on the fact that freed silver ions react with various of the bacterial cell's components. However, the antimicrobial effect achieved in this manner is often moderate and of limited duration as the antimicrobial additives often migrate out of the plastic. This type of application has been described in various patent applications.

DE 10 2008 062 824 A1 describes an antimicrobial wound dressing, DE 10 2008 013 143 A1 describes a silver-containing silane system for coating purposes, DE 10 2007 035 063 A1 describes the use of silver orthophosphate in plastics, and DE 10 2006 006 675 A1 describes the use of sliver-copper nano particles in ceramics.

Also known in the art are polymers that intrinsically have antimicrobial properties, i.e. where the polymer is antimicrobial "as such" without external additives. For instance, what are referred to as contact microbicidal polymers are known from DE 100 24 270. For example, DE 197 09 076 describes antimicrobial plastics prepared through the polymerization of tert-butylaminoethyl methacrylate, and DE 199 21 903 A1 describes copolymers based on tert-butylaminoethyl methacrylate.

Further intrinsically antimicrobial polymers known in the art have quaternary ammonium or phosphonium structures. These are hydrophilic polymers which are usually highly water-compatible as they can swell considerably until they are soluble, have a generally low dimensional stability under heat, and possess insufficient material properties. These polymers are thus unsuitable for use as plastic materials for a wide range of applications. For example, EP 663 409 A1 describes antimicrobial polymers prepared by homo or copolymerising monomers with quaternary phosphorous compounds. These polymers have a wide antimicrobial spectrum and are effective even if contact times are short. It also describes how to prepare an antimicrobial resin, the antimicrobial effect of which is also based on quaternary phosphorous compounds. Polymers obtained by this method are suitable, for instance, for treating contact lenses and contact lens cleaning and care products as well as their storage containers antimicrobially and thus preventing these items from being infested by bacteria and fungi. This is necessary as contact lenses come into direct contact with the cornea of the eye where bacteria and fungi can cause painful inflammations and damage.

Monomers used in preparing the homo and copolymers are disclosed, for example, in DE 10 008 177 A1 and EP 0 611 782 A1. The following is an example of a typical monomer structure (see EP 0 663 409 A1):

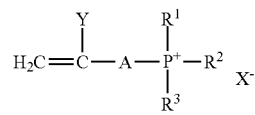

A polymer quat with a polystyrene spine is described by U.S. Pat. No. 4,482,680, and the monomers used therein are based on vinylbenzyl chloride (VBC).

However all of the disclosed plastics have inadequate mechanical properties. In addition, the plastics have high hydrophilicity and low dimensional stability under heat. Furthermore, the neutral intrinsically antimicrobial polymers (that are not based on quaternary compounds) that had been prepared until then tend to undergo oxidation-induced aging processes, which lead to discoloration and a reduction in long-term stability. Due to these inadequate properties, the intrinsically antimicrobial polymers manufactured to date cannot be processed via thermoplastic molding methods (plastics engineering techniques such as extrusion, injection molding, etc.) into products that meet the demands placed on conventional polymer materials and can be used in a wide range of applications.

US 2006/228966 A1 contains a description of how to apply an antimicrobial poly(diemthylamino)-methylstyrene film to surfaces via chemical vapor deposition. The document does not disclose thermoplastic treatment or a glass temperature of 60 to 200° C.

US 2006/234059 A1 describes a modified electrode that includes a functional organic substance such as poly(N,N-dibutylamino-methylstyrene) or poly(N,N-diethylaminomethylstyrene). The document does not deal with polymers that can be processed thermoplastically.

U.S. Pat. No. 4,447,580 A relates to a resin composition containing a polymer (A) such as N-isopropylaminomethylstyrene, N-t-butylaminomethylstyrene or N-pentylaminomethylstyrene as well as a polymer (B) with an electron-attracting group and a neighboring ethylenic double bond, wherein the composition is cross-linked and cured at higher temperatures. The resin obtained as a result cannot be processed thermoplastically.

The state of the art thus fails to describe products that can be processed antimicrobially or thermoplastically.

OBJECTS OF THE INVENTION

Against this backdrop, the object of the invention was to prepare polymers having an antimicrobial effect—preferably an intrinsic antimicrobial effect—and a dimensional stability under heat sufficient for them to be used as materials. The aim is to enable them to be further processed into molded articles via thermoplastic molding methods without having to apply them to a substrate. Another goal is to prepare polymers having the desired properties—in particular adequate dimensional stability under heat, thermal moldability at a temperature of from 75 to 350° C. as well as a low degree of water absorption—over a long period of time, even when constantly in contact with water. A further object is to make polymers available that are as impervious to the effects of external forces as possible, e.g. less easily scratched The ultimate goal is the ability to renounce adding external agents having an antimicrobial effect such as silver ions or Trichlosan, etc. in order to achieve the antimicrobial effect.

Quite unexpectedly, the huge challenges faced in preparing appropriate antimicrobial plastics were mastered by polymerizing or copolymerizing specific monomers to antimicrobial polymers. The polymers as per the invention have an antimicrobial effect and can be processed thermoplastically. In addition, the preferred required material characteristics and the preferably low level of water absorption continue to be present.

SUBJECT MATTER OF THE INVENTION

The subject matter of the invention is thus an antimicrobial polymer obtainable by polymerizing a monomer, wherein the monomer is represented by the structural formulas IIa to IIc or blends thereof

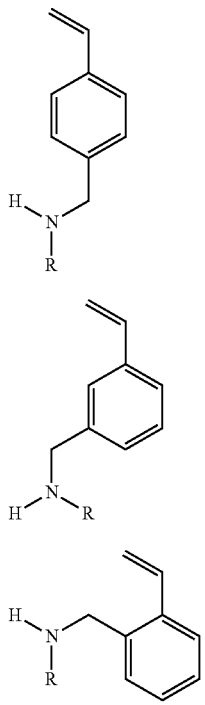

and wherein the residue R is an organic residue—preferably ethyl, propyl, butyl, pentyl, hexyl and heptyl, cyclopropyl, cyclobutyl, cyclopentyl or cyclohexyl isopropyl, sec. butyl, iso-butyl, tert-butyl, 2-pentyl(sec. pentyl), 3-pentyl, 2-methyl-butyl, 3-methyl-butyl(isopentyl), 3-methyl-but-2-yl, 2-methylbut-2-yl, 2,2-dimethylpropyl(neopentyl), 2-methylpentyl, 3-methylpentyl, 2,3-dimethylbutyl, 2,2-dimethylbutyl(neohexyl) or 3-ethylpentyl—and wherein the polymer's glass temperature $T_G$ is 60° C. to 200° C. and wherein preferably, the polymer can be processed thermoplastically.

The invention also describes a method for the preparation of an antimicrobial polymer according to the invention comprising the following steps:
(I) providing a monomer in accordance with formula IIa to IIc;
(Ii) if necessary, providing at least one additional monomer, and
(Iii) polymerizing the monomers by or without adding a polymerization initiator.

The subject matter of the invention also includes an antimicrobial polymer blend containing an antimicrobial polymer obtainable by polymerizing a monomer having a structure according to formula I $$A\text{-}B\text{-}C'\text{-}D \qquad (I),$$

whereby
A is a radically polymerizable group of the formula —$CR^{V1}$=$CR^{V2}R^{V3}$, wherein $R^{V1}$, $R^{V2}$ and $R^{V3}$, independently of each other, are hydrogen, methyl, chloride, cyano or ester groups,
B is an aromatic spacer,
C' is an aliphatic spacer of the formula —$CR^{S1}R^{S2}$—, wherein $R^{S1}$ and $R^{S2}$, independently of each other, are hydrogen or methyl, and
D is an amine of the formula —$NR^{41}R^{42}$, wherein $R^{41}$ is a non-aromatic group with 2 to 7 carbon atoms, and $R^{42}$ is hydrogen, methyl or a non-aromatic group with 2 to 7 carbon atoms, wherein
$R^{41}$ and $R^{42}$ are connected to each other and form a ring together with the nitrogen,
wherein the ring includes 3 to 6 carbon atoms, wherein the ring formed can carry up to 4 methyl groups,
Wherein the polymer's glass temperature $T_G$ is preferably 60° C. to 200° C.;
and/or
a copolymer obtainable by reacting at least one monomer of the formula I, wherein groups A, B, C' and D are defined as set out above and at least one further monomer, preferably comprising
a) alkaline monomers and/or
b) acidic monomers and/or
c) associating monomers and/or
D) standard monomers,
Wherein the copolymer's glass temperature $T_G$ is preferably 65° C. to 230° C.,
and at least one further polymer (the additional blend polymer shall be referred to as "BLEPO").

In this application, in the general formula I, the aliphatic spacer shall be designated C', whereas "C" shall otherwise represent a carbon atom.

The invention also describes the use of a polymer according to the invention or of a polymer blend according to the invention for antimicrobial treatment, the preparation of antimicrobial products, or the production of antimicrobial composite elements, wherein the polymer or polymer blend can preferably be processed thermoplastically.

Determining Antimicrobial Activity

Within the scope of the present application, the antimicrobial property is usually determined by applying a method that is based on the Japanese standard JIS Z 2801:2000. The test microorganism used in the experiments is preferably the pathogenic germ *Staphylococcus aureus* (preferably the standard germ and not the multi-resistant ATCC 6538).

Antimicrobial activity is usually determined by comparing the growth of *Staphylococcus aureus* on reference surfaces to that on sample material.

Empty petri dishes are used as reference material. The samples consist of petri dishes (90 mm in diameter) coated with about 0.250 to 0.750 g of the corresponding polymer. The coating is applied according to the following procedure: The polymers are dissolved in a suitable solvent. The polymer solution is placed on the petri dish, after which the solvent is evaporated in a vacuum drying cabinet. Three reference plates and three sample plates are used in each test series in order to determine the surface germ content after incubation.

All plates are inoculated with 400 µl of *Staphylococcus aureus* vaccination suspension that is set to a germ content of 5-8·105 CFU/ml.

The inoculated plates are covered with a sterile PP film in order to avoid evaporation. Immediately after the inoculation, the three sample plates and three reference plates are placed in an incubation cabinet and incubated for 24 hours at 35° C. and 90% humidity.

To determine the germ concentration of the inoculation solution (initial germ content) three reference plates are washed immediately after inoculation by placing 10 ml of SCDLP bouillon in the petri dish. The film is flipped using sterile tweezers and repeatedly flooded and flushed using a 1 ml pipette. The petri dish is waved in a figure eight before pipetting 1 ml of the rinsing solution into the first dilution level. Once the thinning series has been set up, the living germ content is determined using the drop plate method. The drop plate method entails applying—in duplicate—5 drops of 10 µl each onto a plate count agar plate in every sector of the dilution level. The plates are incubated for 24 hours at 37° C.

The rinsing and determination of the living germ count on the reference and test plates after the incubation is performed applying the procedure followed to determine the initial germ content. As regards the test plates, besides raising the detection limit, the germ content of the direct rinsing solution is determined using the pour plate method. To this end—also in duplicate—1 ml of the solution is placed in an empty petri dish, over which liquid PC agar, tempered at 45° C., is poured. By waving it in a figure eight, the bacteria are distributed in the agar. The plates are incubated for 48 hours at 37° C.

After the incubation, the colonies in the petri dish are counted. It is assumed that each germ has turned into a visibly colony. After the incubation, the colonies can be discerned by the naked eye. If necessary, a light table can be used to make the germs more visible.

Based on the volume of the inoculation solution and the thinning ratios applied, one can deduce the living germ count of the microorganisms per volumetric unit (i.e. per ml) of inoculation solution. The calculation is performed based on a weighted arithmetic average, applying the following formula:

$$\overline{c} = \frac{\sum c}{n_1 \cdot 1 + n_2 \cdot 0.1} \cdot d$$

where
$\overline{c}$ represents the weighted arithmetic average,
$\Sigma c$ represents the sum of the colonies of all petri dishes or sectors used as a basis for the calculation,
$n_1$ represents the number of the petri dishes or sectors of the lowest evaluable dilution level,
$n_2$ represents the number of petri dishes or sectors of the next higher dilution level, and
d represents the lowest evaluated dilution level.

When using the pour plate method, petri dishes with up to 300 CFU can be counted. When using the drop plate method, only plates with up to 150 CFU per sector can be counted.

The thinning factor $F_1$ must be maintained when determining the living germ count per ml. This is the sum of the volume of the SCDLP bouillon and the volume of the bacterial suspension on the inoculated plate.

$$F_1 = \frac{10 \text{ ml} + 0.4 \text{ ml}}{0.4 \text{ ml}} = 26$$

whereby
$F_1$ represents the thinning factor of the SCDLP bouillon.

This results in the following formula, which is applied to determine the total germ count on the inoculated sample or reference plates using the pour plate method:

$$KbE = \frac{\sum c}{n_1 \cdot 1 + n_2 \cdot 0.1} \cdot d \cdot F_1$$

When using the drop plate method, a further tinning factor becomes relevant, as a quarter of a plate is only inoculated with 50 µl, i.e. 0.05 ml. To deduce the germ content per ml, 0.05 ml has to be scaled up to 1 ml by multiplying it by 20.

$$F_2 = 26 \cdot 20$$

whereby
$F_2$ represents the thinning factor used to obtain the CFU in the drop plate method per ml.

Accordingly, the total germ count of the inoculated sample and reference plates is calculated for the drop plate method taking account of all thinning factors applying the following formula:

$$KbE = \frac{\sum c}{n_1 \cdot 1 + n_2 \cdot 0.1} \cdot d \cdot F_2$$

To calculate antimicrobial activity, in every test series, the individual results of the living germ count for the plates are combined to form a simple arithmetic mean, based on which the $\log_{10}$ reduction between the sample and reference plates is determined.

The calculation is performed by applying the following formula:

$$\log_{10} \text{reduction} = \log_{10}(KG)_{Ref(x)} - \log_{10}(KG)_{Pr(x)}$$

whereby
$(KG)_{Ref(x)}$ represents the CFU on the reference plates at time instance x
$(KG)_{Pr(x)}$ represents the CFU on the sample plates at time instance x The antimicrobial activity of the polymer according to the invention is preferably indicated by the $\log_{10}$ reduction after 24 h contact time. The $\log_{10}$ reduction is preferably at least log 2.0 CFU/ml after 24 h. Especially preferred is a log reduction that leads to a residual germ content of log 1 or 10 colony-forming units (the method's detection limit).

According to JIS Z 2801:2000, antimicrobial activity exists if the log reduction is at least 2.0 after 24 hours of exposure. If there are no countable colonies on the agar plates of the samples at the lowest dilution level using the pour plate method, the result is stated as <10 CFU/ml, in line with the requirement in the test standard.

DETAILED DESCRIPTION OF THE INVENTION

The antimicrobial polymer of the invention is obtainable by polymerizing a monomer, whereby the monomer is represented by the structural formulas IIa to IIc or mixtures thereof,

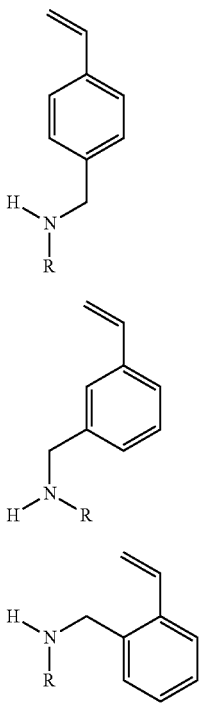

and wherein the residue R is ethyl, propyl, butyl, pentyl, hexyl and heptyl, cyclopropyl, cyclobutyl, cyclopentyl or cyclohexyl isopropyl, sec-butyl, iso-butyl, tert-butyl, 2-pentyl(sec. pentyl), 3-pentyl, 2-methyl-butyl, 3-methyl-butyl (isopentyl), 3-methyl-but-2-yl, 2-methylbut-2-yl, 2,2-dimethylpropyl(neopentyl), 2-methylpentyl, 3-methylpentyl, 2,3-dimethylbutyl, 2,2-dimethylbutyl(neohexyl) or 3-ethylpentyl,
wherein the antimicrobial polymer's glass temperature is 60° C. to 200° C. and wherein preferably, the polymer can be processed thermoplastically.

A monomer according to formula IIa is preferred.

A mixture of two monomers, preferably of the monomers according to formulas IIa and IIb, is an alternative preference.

In a preferred embodiment, the polymerization of the radically polymerizable vinyl group may be a photochemically initiated radical polymerization. Photochemically initiated polymerization generally involves the use of a compound that undergoes a photo reaction when it absorbs light, preferably in the range of 300 to 450 nm. This reaction generates the reactive species that reacts with the radically polymerizable group, thereby initiating the polymerization.

In an especially preferred embodiment, the polymerization of the radically polymerizable group may be a thermally initiated radical polymerization with or without an initiator. The radical polymerization may be initiated purely thermally (without an initiator) or via peroxide initiators, azo-initiators, redox systems or photochemically.

Preferred vinyl group polymerization initiators are described as "preferred initiators" in the following section.

Preferred Group R Embodiments in Formulas IIa to IIc

R can generally be an organic residue. R is preferably isopropyl, sec-butyl, iso-butyl, tert-butyl, 2-pentyl(sec. pentyl), 3-pentyl, 2-methylbutyl, 3-methylbutyl(isopentyl), 3-methyl-but-2-yl, 2-methylbut-2-yl, 2,2-dimethylpropyl (neopentyl), 2-methyl-3-pentyl, 3-methyl-3-pentyl, 2,3-dimethylbutyl, 2,2-dimethylbutyl(neohexyl) or 3-ethyl-3-pentyl. More preferably, R is isopropyl, sec. butyl, iso-butyl, tert-butyl, 3-methyl-but-2-yl, 2-methylbut-2-yl, 2-methyl-3-pentyl, 3-methyl-3-pentyl, 2,3-dimethylbutyl or 3-ethyl-3-pentyl. Even more preferably, R is tert-butyl, 2-methylbut-2-yl, 3-methyl-3-pentyl or 3-ethyl-3-pentyl. Very particularly preferably, R is 2-methylbut-2-yl. Very particularly preferably, R is 3-methyl-3-pentyl. Very particularly preferably, R is 3-ethyl-3-pentyl. Especially preferably, R is tert-butyl.

Especially preferred is formula IIa where R=tert-butyl. The polymer obtainable from this monomer is abbreviated to TBAMS and is an especially preferred antimicrobial polymer according to the invention.

An alternative aspect of the invention involves obtaining the antimicrobial polymer by polymerizing via a monomer that is represented by the following formula I:

A-B-C'-D     (formula I),

Wherein A, B, C' and D are defined as set out below in formula I. All of the commentary on preferred embodiments of the polymers according to formula II, e.g. the glass temperature, also applies to the polymers according to formula I.

Preferred Embodiments Concerning the Glass Temperature

The glass temperature of the antimicrobial polymer according to the invention is customarily 60° C. to 200° C., preferably 70° C. to 180° C., especially preferably 75° C. to 140° C. and very especially preferably 80° C. to 130° C. In alternative preferred embodiments, the glass temperature is 85° C. to 125° C. or 90° C. to 120° C. Mixtures of these temperature ranges are also possible. The glass temperature can be set by a person skilled in the art by selecting the process parameters accordingly, i.e. the starting materials and the process parameters such as the polymerization temperature, polymerization time, type and amount of catalyst are selected to ensure that the desired glass temperature can be reached.

The glass temperature generally has a significant impact on processability as well as on the material properties of a polymer. The glass temperature is the temperature at which an essentially amorphous polymer transitions from solid, glassy or energy elastic state to a viscoelastic, rubbery or entropy plastic state, or vice-versa. Below the glass temperature, the polymer is essentially hard and brittle (glassy) whereas above this temperature, it begins to become viscous and viscoelastic. The terms "glass temperature" and "glass transition temperature" are often used synonymously.

The glass temperature of the polymers according to the invention is preferably determined through dynamic difference calorimetry (DSC) measurements. For the purpose, preferably about 10 mg of polymer are measured into a 40 µl aluminum DSC cauldron, which is used in the measurement cell of a METTLER Toledo 821$^e$. Thereafter, a heating/cooling program is launched, which is divided into three identical cycles. A cycle is structured as follows: It begins by heating from 25° C. to 250° C. at a rate of 10° C./min, followed by cooling from 25° C. to 250° C. at a rate of −10° C./min. This is followed by the second and third cycles. The glass temperature is determined by establishing the mean of the glass transition temperatures calculated for all heating steps.

These are the settings preferred for the Mettler Toledo 821:

Nitrogen flow: 8.3 N/h
Nitrogen cooling, no gas controller
Module standby temperature: 20° C.
Ceramic sensor; SRS5 high
Star Excellence software Version 9.10, routine window, DSC evaluation Calibration is preferably performed using the in sample (6.27 mg) dated Dec. 3, 2005 supplied by the manufacturer.

In a preferred embodiment, the antimicrobial polymer is a homopolymer.

In an especially preferred embodiment, the antimicrobial polymer is a homopolymer obtainable by polymerizing the compound according to formula IIa.

The compounds of formulas IIa to IIc can be prepared by reacting the compound of the formula $H_2C\!=\!CH$-phenylene-$CH_2$—Cl with $H_2N$—R. In formulas IIa to IIc and in the formula $H_2N$—R, R is preferably defined as set out above.

A correspondingly preferred monomer is prepared, for example, as follows: 200 ml of water and 42 g (1.05 mol) NaOH are placed in a 1,000 ml flask and once they have been completely dissolved, they are added to 1.05 mol of the corresponding amine. While stirring, the flask is heated to 60-85° C. and dripped into a solution of 53.42 g (0.35 mol) chlorine methylstyrene and 150 ml of TI-IF for about 75 minutes. Once completely dripped in, the reaction flask is left in the oil bath for a total reaction period of 4-120 h under constant stirring. The reaction time and reaction temperature depend on the amine used. The purification can be performed by vacuum distillation.

In a preferred embodiment, the polymer of the present invention is a homopolymer, preferably a homopolymer that is made up of monomers IIa, IIb or IIc or mixtures thereof. Homopolymers are polymers, the macromolecules of which are exclusively made up of monomers of the same type.

Preferred Embodiments of the Copolymers According to the Invention

In another preferred embodiment, the antimicrobial polymer according to the present invention is a copolymer. The copolymer of the invention is customarily obtainable by copolymerizing a monomer of formula IIa, IIb or IIc with another monomer. The copolymer according to the invention is thus preferably obtainable by reacting at least one monomer pursuant to formulas IIa to IIc with at least one further monomer, wherein said further monomer preferably comprises:
a) alkaline monomers and/or
b) acidic monomers and/or
c) associating monomers and/or
d) standard monomers,
wherein the copolymer's glass temperature $T_G$ is 65° C. to 230° C., preferably 70° C. to 200° C., especially preferably 75° C. to 160° C. and particularly especially preferably 80° C. to 150° C. In further preferred embodiments, the copolymer's glass temperature can be 85° C. to 145° C., 90° C. to 140° C. or 95° C. to 135° C. Mixtures of these temperature ranges are also possible.

Preferred embodiments of the further monomers a to d, which may be used to prepare the copolymers according to the invention:

Alkaline monomers (a) are generally compounds comprising both a polymerizable as well as an alkaline group. Alkaline monomers (a) are preferably monomers with at least one primary, secondary or tertiary amine and/or monomers with at least one heterocyclical nitrogen-containing aromatic. Examples of preferred alkaline monomers are vinylimidazoles such as 1-vinylimidazole, 2-methyl-1-vinylimidazole, N-vinyloxazolidone, N-tert-butylaminoethyl methacrylate, N,N-dimethylaminoethyl methacrylate, N,N-diethylaminoethyl methacrylate, N,N-diisopropylaminoethyl methacrylate, 2-vinylpyridine, 3-vinylpyridine, 4-vinylpyridine, N-vinyltriazole, aminalkyl vinyl ether, and mixtures thereof.

More preferred are N-tert-butylaminoethyl methacrylate, N,N-dimethylaminoethyl methacrylate, N,N-diethylaminoethyl methacrylate, N,N-diisopropylaminoethyl methacrylate, 2-vinylpyridine, 3-vinylpyridine, 4-vinylpyridine, and mixtures thereof, in particular N-tert-butylaminoethyl methacrylate, 2-vinylpyridine, 3-vinylpyridine, 4-vinylpyridine and mixtures thereof.

The alkaline monomers are usually used in an amount of 0 to 95 mol %, preferably 10 to 80 mol %, more preferably 20 to 70 mol % and even more preferably 25 to 60 mol %, relative to the total monomer content.

The acidic monomers (b) are preferably monomers having a polymerizable group and at least one free acid group or a group from which an acid can easily be formed, e.g. an acid anhydride. The acidic monomers are preferably selected from acrylic acid, chlorine acrylic acid, cyanoacrylic acid, methacrylic acid, itaconic acid and their anhydride, mesaconic acid, citraconic acid, crotonic acid, fumaric acid, maleic acid, vinylbenzoic acid and their isomers, cinnamic acid, stilbene dicarboxylic acid, vinylphosphonic acid, vinylbenzyl phosphonic acid, vinylbenzyl sulfonic acid, vinylsulfonic acid, 2-Styrene sulfonic acid, 3-Styrene sulfonic acid, 4-Styrene sulfonic acid, 2-Styrene phosphonic acid, 3-Styrene phosphonic acid, 4-Styrene phosphonic acid and mixtures thereof.

Especially preferred are acrylic acid, chlorine acrylic acid, cyanoacrylic acid, methacrylic acid, itaconic acid and their anhydride, mesaconic acid, citraconic acid, fumaric acid, maleic acid, vinylbenzoic acid and their isomers, cinnamic acid, vinylbenzyl phosphonic acid, vinylbenzyl sulfonic acid and mixtures thereof, especially chlorine acrylic acid, cyanoacrylic acid, methacrylic acid, itaconic acid and their anhydride, mesaconic acid, citraconic acid, vinylbenzoic acid and their isomers as well as mixtures thereof.

The acidic monomers are usually used in an amount of 0 to 50 mol %, preferably 1 to 40 mol %, more preferably 2 to 30 mol % and even more preferably 3 to 20 mol %, relative to the total monomer content.

The associating monomers (c) are preferably monomers having a polymerizable group which can associate with the monomers of formula I as well as among each other. Such an associating bond may preferably be based on a strong hydrogen bridge bond or strong dipole-dipole interactions. The associating monomers are preferably selected from acrylonitrile, methacrylonitrile, alkyl-substituted acrylamides such as acrylamide, methacrylamide, N,N-dimethylacrylamide, N-ethacrylamide, N-tert-butylacrylamide, vinyl methylacetamide, N-tert-octylacrylamide, methyl cyanoacrylate, dicyanoethelyene, 1-nitrovinylene, 1-nitro-1-methylvinylidene, vinylpyrrolidone, vinylcaprolactam and vinylbenzonitrile and their isomers as well as mixtures thereof.

Especially preferred are acrylonitrile, methacrylonitrile, methyl cyanoacrylate, dicyanoethelyene, vinylpyrrolidone, vinylcaprolactam, vinylbenzonitrile and their isomers as well as mixtures thereof, especially acrylonitrile, methacrylonitrile and vinylbenzonitrile and their isomers as well as mixtures thereof.

The associating monomers are present in a range of 0 to 95 mol %, preferably 10 to 85 mol %, more preferably 15 to 80 mol % and even more preferably 20 to 70 mol %, relative to the total monomer content.

The standard monomers (d) preferably contain a polymerizable group that enables copolymerization with the described monomer of formulas IIa to IIc.

Preferably, the standard monomers are selected from vinyl monomers of the general formula III

Y may, for example, be hydrogen, alkyl (preferably methyl, ethyl, tert-Butyl), aryl, halogen, cyano or nitro.

In this application, the variable X is defined as an organic residue hereinafter. This organic residue may be at least one heteroatom, preferably selected from the group consisting of oxygen, sulfur, nitrogen, phosphorus, fluorine, chlorine and bromine silicon and may be aromatic and/or aliphatic.

Examples of very suitable single-bond organic residue X are
- alkyl residues, preferably having 2 to 20, more preferably 2 to 15 and especially preferably 2 to 12 carbon atoms;
- cycloalkyl residues, preferably having 3 to 20, more preferably 4 to 15 and especially preferably 5 or 8 carbon atoms;
- aryl residues, preferably having 6 to 28, more preferably 6 to 20 and especially preferably 6 to 14 carbon atoms;
- alkyl ether, cycloalkylether and arylether residues (—O residue), wherein the residue is preferably selected from the aforementioned alkyl residues, cycloalkyl residues and aryl residues;
- carboxylic alkylester residues (—O—CO residue or —CO—O residue), preferably having 1 to 10, more preferably 1 to 12 and especially preferably 1 to 8 carbon atoms in the alkyl residue;
- carboxylic alkylester residues (—O—CO residue or —CO—O residue), preferably having 3 to 14, more preferably 4 to 9 and especially preferably 5 to 7 carbon atoms in the cycloalkyl residue;
- carboxylic arylester residues (—O—CO residue or —CO—O residue), preferably having 6 to 28, more preferably 6 to 22 and especially preferably 6 to 10 carbon atoms in the aryl residue;
- carboxylic amide residues (—NR—CO residue), wherein the residue is preferably selected from the group consisting of the aforementioned alkyl residues, cycloalkyl residues, aryl residues and hydrogen atom, or wherein the two residues are cyclically bonded to each other, resulting in preferably one ring having four, five or six links; and
- silyl residues (—SiH$_2$R, —SiHR$_2$ or —SiR$_3$), wherein the residue R is preferably selected from the group consisting of the aforementioned alkyl residue, cycloalkyl residues and aryl residues R, wherein 2 or 3 residues R may also be cyclically bonded to each other; and
- silyl alkyl residues (—SiH$_2$(OR), —SiH(OR)$_2$, —Si(OR)$_3$, —SiHR(OR), —SiR2(OR), or —SiR(OR)$_2$), wherein the residue R is preferably selected from the group consisting of the aforementioned alkyl residues, cycloalkyl residues and aryl residues R, wherein 2 or 3 residues R may also be cyclically bonded to each other.

The residues may be substituted or unsubstituted, preferably unsubstituted.

Examples of very suitable substituents for the substituted residues are halogen atoms—preferably fluorine, chlorine and bromine, especially fluorine and chlorine, nitrile groups, nitro groups, ether residues (—O residue), ester residues (—O—CO residue or —CO—O residue) and thiole groups. Here, the residues are of the significance set out above.

The following is a selection of representatives of examples of aromatic vinyl monomers: o-, m- or p-methylstyrene, methylstyrene, 2,6-dimethylstyrene and 2,4-dimethylstyrene, methyl-o-methylstyrene, methyl-m-methylstyrene, methyl-p-methylstyrene, 2,4,6-dimethylstyrene, methyl-2,6-dimethylstyrene, methyl-2,4-dimethylstyrene, o-, m- or p-chlorostyrene, 2,6-dichlorostyrene 2,4-dichlorostyrene, chloro-o-chlorostyrene, chloro-m-chlorostyrene, chloro-p-chlorostyrene, 2,4,6-trichlorostyrene, chloro-2,6-dichlorostyrene, chloro-2,4-dichlorostyrene, o-, m- or p-tert-butylstyrene, o-, m or p-methoxystyrene, o-, m- or p-chloromethylstyrene, o-, m- or p-bromomethylstyrene, silyl-substituted styrene derivates, inden, vinylnaphthaline or heteroaromatic vinyl monomers such as vinylpyrrolidone and the like.

Furthermore, aliphatic vinyl monomers should be mentioned by way of example. Selected examples are: ethylene, propylene, 1-butene, 1-pentene, 1-hexene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 1-octene, 1-decene, 1-dodecene, 1-tetradecene, 1-hexadecene, 1-octadecene, cyclohexene, 4-methyl-1-pentene, vinylcyclohexene, octene, norbornene and the like.

Vinyl chloride and/or vinyl acetate may also be used as preferred standard monomers (d).

The standard monomers (d) are more preferably selected from ethylene, butadiene, isoprene, chloroprene, substituted styrene, methacrylic ester, acrylic ester, vinyl ether (e.g. ethyl vinyl ether, isobutyl vinyl ether, tert-butyl vinyl ether, methyl vinyl ether, butyl vinyl ether, cyclohexyl vinyl ether), vinyl carbazole, vinyl thioether, vinyl ester, vinyl cyclohexene vinyl methyl chloride, vinylidene fluoride, vinyl acetate, vinyl silane, vinyl chloride, vinyl fluoride, vinylidene chloride vinyl benzyl chloride, vinyl benzyl bromide, diesters of fumaric acid, diamides of fumaric acid, imides of maleic acid and mixtures thereof.

Especially preferred are butadiene, isoprene, chloroprene, substituted styroene, vinyl ether (e.g. ethyl vinyl ether, isobutyl vinyl ether, tert-butyl vinyl ether, methyl vinyl ether, butyl vinyl ether, cyclohexyl vinyl ether), vinyl carbazole, vinyl ester, vinylidene fluoride, vinyl acetate, vinyl silane, vinyl chloride, vinyl fluoride vinylidene chloride, vinyl benzyl chloride, vinyl benzyl bromide, diesters of fumaric acid, diamides of fumaric acid, imides of maleic acid and mixtures thereof; especially preferred are butadiene, isoprene, chloroprene, vinyl chloride, methacryl ester, vinyl carbazole and mixtures thereof.

The standard monomers are present in a range of 0 to 70 mol %, preferably 2 to 55 mol %, more preferably 3 to 40 mol %, even more preferably 4 to 30 mol % and even more especially even more preferably 4 to 25 mol %, relative to the total monomer content.

It may be in the nature of the "further" monomers that a monomer can be broken down into several of the classes a to d. Therefore, to distinguish the monomers, each of them may only be assigned to one of groups a to d. For example, if a monomer X is already present as an associating monomer in the copolymer according to the invention or in the polymer blend according to the invention, it may not be used as a standard monomer as well.

These copolymers may be alternating copolymers, block copolymers or statistical copolymers. The term "copolymers" shall also comprise the joint polymerization of three or more different monomers, i.e. for example also terpolymers.

It was unexpectedly found that the addition of at least one further monomer from the aforementioned groups of further monomers results in improved processability (e.g. reduced adhesion to the metal surfaces of the helices during extrusion) as well as improved material properties (dimensional stability under heat and reduced water absorption) of the resulting copolymer, while maintaining outstanding antimicrobial properties.

It was unexpectedly found that the use of the described preferred comonomers improved the processability of the preferably selected (described) monomers and increased their glass temperature, whereas the antimicrobial properties were surprisingly not reduced (according to the described test method).

As described above, the copolymers of the invention are obtainable by reacting the monomers of the invention with further monomers. In a preferred embodiment, the copolymers are preferably obtainable by reacting 1 to 99 mol %, more preferably 15 to 95 mol % and even more preferably 40 to 90 mol % of the monomers of the invention according to formulas IIa to IIc with the further monomers of the alkaline monomer (a) and/or acidic monomer (b) and/or associating monomer (c) and/or standard monomer (d) classes The further monomers are used in the copolymer in an amount of preferably 1 to 99 mol %, more preferably 5 to 70 mol % and even more preferably 10 to 70 mol %.

Especially Preferred Embodiments of the Copolymers According to the Invention

In an especially preferred embodiment, the antimicrobial polymer according to the invention is a copolymer, obtainable by polymerizing a monomer of formulas IIa to IIc, particularly of formula IIa, with acrylonitrile. The copolymer is preferably obtainable by reacting 1 to 99 mol %, more preferably 30 to 95 mol % and especially preferably 40 to 90 mol % monomers according to formulas IIa to IIc, particularly formula IIa and 1 to 99 mol %, more preferably 5 to 70 mol %, and especially preferably 10 to 60 mol % with acrylonitrile. In the present embodiment, the polymer according to the invention may solely have been prepared from monomers of formulas IIa to IIc, particularly formula IIa, and acrylonitrile. If necessary, 0 to 60 mol %, preferably 0 to 40 mol %, of the monomers described above may be added to the polymerization.

In an especially preferred embodiment, the antimicrobial polymer according to the invention is a copolymer, obtainable by polymerizing a monomer of formulas IIa to IIc, particularly of formula IIa, with methacrylonitrile. The copolymer is preferably obtainable by reacting 1 to 99 mol %, more preferably 30 to 95 mol % and especially preferably 40 to 90 mol % monomers according to formulas IIa to IIc, particularly formula IIa and 1 to 99 mol %, more preferably 5 to 70 mol %, and especially preferably 10 to 60 mol % with methacrylonitrile. In the present embodiment, the polymer according to the invention may solely have been prepared from monomers of formulas IIa to IIc, particularly formula IIa, and methacrylonitrile. If necessary, 0 to 60 mol %, preferably 0 to 30 mol %, of the monomers described above may be added to the polymerization.

In an especially preferred embodiment, the antimicrobial polymer according to the invention is a copolymer, obtainable by polymerizing a monomer of formulas IIa to IIc, particularly of formula IIa, with vinylpyridine, particularly 4-vinylpyridine. The copolymer is preferably obtainable by reacting 1 to 99 mol %, more preferably 30 to 95 mol % and especially preferably 40 to 90 mol % monomers according to formulas IIa to IIc, particularly formula IIa and 1 to 99 mol %, more preferably 5 to 70 mol %, and especially preferably 10 to 60 mol % with vinylpyridine, particularly 4-vinylpyridine. In the present embodiment, the polymer according to the invention may solely have been prepared from monomers of formulas IIa to IIc, particularly formula IIa, and vinylpyridine, particularly 4-vinylpyridine. If necessary, 0 to 30 mol % of the monomers described above may be added to the polymerization.

In an especially preferred embodiment, the antimicrobial polymer according to the invention is a copolymer, obtainable by polymerizing a monomer of formulas IIa to IIc, particularly of formula IIa, with acrylic acid and/or methacrylic acid and/or p-vinylbenzoic acid. The copolymer is preferably obtainable by reacting 1 to 99 mol %, more preferably 30 to 97 mol % and especially preferably 70 to 96 mol % monomers according to formulas IIa to IIc, particularly formula IIa and 1 to 99 mol %, more preferably 3 to 70 mol %, and especially preferably 4 to 30 mol % with acrylic acid and/or methacrylic acid. In the present embodiment, the polymer according to the invention may solely have been prepared from monomers of formulas IIa to IIc, particularly formula IIa, and acrylic acid and/or methacrylic acid. If necessary, 0 to 30 mol % of the monomers described above may be added to the polymerization.

In an especially preferred embodiment, the antimicrobial polymer according to the invention is a copolymer, obtainable by polymerizing a monomer of formulas IIa to IIc, particularly of formula IIa, with vinylbenzoic acid, particularly 4-vinylbenzoic acid. The copolymer is preferably obtainable by reacting 1 to 99 mol %, more preferably 30 to 95 mol % and especially preferably 40 to 90 mol % monomers according to formula II, particularly formula IIa and 1 to 99 mol %, more preferably 5 to 70 mol %, and especially preferably 10 to 60 mol % with vinylbenzoic acid, particularly 4-vinylbenzoic acid. In the present embodiment, the polymer according to the invention may solely have been prepared from monomers of formula II, particularly formula IIa, and vinylbenzoic acid, particularly 4-vinylbenzoic acid. If necessary, 0 to 30 mol % of the monomers described above may be added to the polymerization.

Preferred Initiators

The polymers according to the invention are generally prepared by polymerizing the described monomers. Preferably, initiators are added to the polymerization reaction.

These initiators are preferably selected from the class of peroxides, disulfides, tetrazenes, azo compounds, acrylalkyl sulfonyl peroxides, diperoxyketales and mixtures thereof.

For example, suitable peroxides are didekanoyl peroxide, 2,5-dimethyl-2,5-di(2-ethylhexanoylperoxy)hexane, tert-amylperoxy-2-ethylhexanoate, dibenzoylperoxide, tert-butylperoxy-2-ethylhexanoate, tert-butylperoxydiethylacetate, tert-butylperoxy-diethylisobutyrate, 1,4-di(tert-butylperoxycarbonyl)cyclohexane as an isomer mixture, tert-butylperisononanoate, 1,1-di-(tert-butylperoxy)-3,3,5-trimethylcyclohexane, 1,1-di-(tert-butylperoxy)-cyclohexane, methyl-isobutylketonperoxide, tert-butylperoxyisopropylcarbonate, 2,2-di-(tert-butylperoxy)butane or tert-butylperoxyacetate; tert-butylperoxybenzoate, di-tert-amylperoxide, dicumylperoxide, the isomeric di-(tert-butylperoxyisopropyl)benzoles, 2,5-dimethyl-2,5-di-tert-butylperoxyhexane, tert-butylcumylperoxide, 2,5-dimethyl-2,5-di(tert-butylperoxy)-hex-3-ine, di-tert-butylperoxide, 1,3-diisopropylbenzene monohydroperoxide, cumolhydroperoxide or tert-butylhydroperoxide.

Examples of suitable initiators of the azo compounds are 2,2'-azobis(isobutyronitrile), 2,2'-azobis(2-methylpropionamidine)dihydrochloride and 2,2'-azobis(4-methoxy-2,4-dimethylvaleronitrile), azodi(cyclohexylcarbonitrile), 2,2'-azobis{2-methyl-N-[1,1-bis(hydroxymethyl)-2-hydroxyethl]propionamide}, 2,2'-azobis[2-methyl-N-(2-hydroxyethyl)propionamide], 2,2'-azobis[N-(2-carboxyethyl)-2-methylpropionamidine]hydrate, 2,2'-azobis[2-(2-imidazoline-2-yl)propane]dihydrochloride, 2,2'-azobis[2-(2-imidazoline-2-yl)propane]disulfate-dihydrate, 2,2'-azobis(2-methylpropionamidine)dihydrochloride, 2,2'-azobis{2-[1-(2-hydroxyethyl)-2-imidazoline-2-yl]propane}dihydrochloride, 2,2'-azobis[2-(2-imidazoline-2-yl)propane], 2,2'-azobis(1-imino-1-pyrrolidino-2-ethylpropane)dihydrochloride, 2,2'-azobis(2-cyano-2-butane), dimethyl-2,2'-azobisdimethyl-isobutyrate, 4,4'-azobis(4-cyanopentanoic acid), 2-(tert-butylazo)-2-cyanopropane, 2,2'-azobis(N,N-dimethylene isobutyramidine)dihydrochloride, 2,2'-azo-bis(N,N'-dimethyleneisobutyramine), 2,2'-azobis(2-methyl-N-[1,1-bis(hydroxymethyl)-2-hydroxyethyl]propionamide), 2,2'-azo-bis(2-methyl-N-[1,1-bis(hydroxymethyl)ethyl]-propionamide), 2,2'-azobis[2-methyl-N-(2-hydroxyethyl)propionamide], 2,2'-azobis(iso-butyramide)dihydrate, 2,2'-azobis(2,2,4-trimethylpentane) and 2,2'-azobis(2-methyl-propane).

The initiators, preferably the azo initiators, are usually used in an amount of $10^{-4}$ to $10^{-1}$ mol/l, preferably in an amount of $10^{-3}$ to $10^{-2}$ mol/l.

The initiation of the residue polymerization may also be performed photochemically as described herein below: To this end, a photoinitiator, which is excited via radiation using a light-suitable wavelength, is added to the reaction mixture, and a residue polymerization is initiated.

For example, the following may be used as photoinitiators: benzophenone, 2-methylbenzophenone, 3,4-dimethylbenzophenone, 3-methyl-benzophenone, 4,4'-bis(diethylamino)benzophenone, 4,4'-di-hydroxy-benzophenone, 4,4'-bis[2-(1-propenyl)phenoxy]benzophenone, 4-(diethylamino)benzophenone, 4-(dimethyl-amino)benzophenone, 4-benzoylbiphenyl, 4-hydroxybenzophenone, 4-methylbenzophenone, benzophenone-3,3',4,4'-tetracarboxyldianhydride, 4,4'-bis(dimethylamino)-benzophenone, acetophenone, 1-hydroxycyclohexylphenylketone, 2,2-diethoxyacetophenone, 2,2-dimethoxy-2-phenylacetophenone, 2-benzyl-2-(dimethylamino)-4'-morpholinobutyrophenone, 2-hydroxy-2-methyl-propiophenone, 2-hydroxy-4'-(2-hydroxyethoxy)-2-methylpropiophenone, 3'-hydroxyacetophenone, 4'-ethoxyacetophenone, 4'-hydroxyacetophenone, 4'-phenoxyacetophenone, 4'-tert-butyl-2',6'-dimethylacetophenone, 2-methyl-4'-(methylthio)-2-morpholinopropiophenone, diphenyl-(2,4,6-trimethylbenzoyl)-phosphinoxide, phenylbis(2,4,6-trimethylbenzoyl)phosphinoxide, methyl benzoylformate, benzoin, 4,4'-dimethoxybenzoin, benzoinmethylether, benzoinethylether, benzoinisopropylether, benzoinisobutylether, 4,4'-dimethylbenzene, hexachlorocyclopentadiene, campherchinone or combinations thereof. An amine such as methyl-bis(hydroxyethyl)amine may be used together with the benzophenone derivatives and campherchinone.

Furthermore, these photoinitiators may be combined with the aforementioned azo compounds and peroxides.

In an alternative preferred embodiment of the invention, the light-induced polymerization may also be performed without a starter. In such cases, in step iii of the method of preparing an antimicrobial polymer according to the invention, the polymerization of the monomers can preferably be carried out without adding the polymerization initiator.

Preferred Embodiments in Respect of Physical Properties

In a preferred embodiment, the number average molecular weight of the antimicrobial polymer according to the invention $M_n$ is 4,500 to 2,000,000 daltons, preferably 6,000 to 1,500,000 daltons, more preferably 7,000 to 1,000,000 daltons, even more preferably 8,000 to 500,000 daltons, particularly 10,000 to 200,000 daltons, as determined using gel permeation chromatography.

The formula for calculating the number average molecular weight is as follows:

$$M_n = \frac{\sum N_i M_i}{\sum N_i}$$

wherein $N_i$ represents the number of molecules that have the molecular mass $M_i$.

The molecular weights indicated preferably relate to the homopolymers according to the invention described earlier as well as the copolymers according to the invention described earlier. Furthermore, the molecular weights indicated also relate to the polymer blend described herein below.

In a preferred embodiment of the antimicrobial polymer according to the invention, a compound containing acid groups or a compound forming acid groups is added during or after the polymerization.

In a further preferred embodiment, the water absorption of the antimicrobial polymers according to the invention amounts to a maximum of 35 wt. %, preferably 0.01 wt. % to 25 wt. %, more preferably 0.05 wt. % to 20 wt. %, even more preferably 0.1 wt. % to 15 wt. % and especially preferably 1 to 10 wt. %, relative to the weight of the polymer. For the purposes of the present application, water absorption is measured according to ISO 62:2008 (German version: EN ISO 62:2008). The method set out in item 6.3 "Determining Water Absorption after Immersion in 23° C. Water" is applied to this end.

The problems described in the introductory portion of this application are solved unexpectedly advantageously as a result of the low water absorption of the polymers according to the present invention.

The polymers according to the invention are thus preferably "hydrophobic polymers." In contrast, many of the antimicrobial polymers known from the state of the art are hydrophilic polymers.

In a preferred embodiment, the antimicrobial polymer according to the invention is a thermoplastic. Thermoplastics are generally processable in the melt, i.e. thermoplastically. Pursuant to EN ISO 472:2001, thermoplastics are defined as polymers that are softened repeatedly at a temperature of a range typical for them, cure upon cooling, and can be reshaped to articles repeatedly by flowing (e.g. as an extrudate) when in softened state. "Thermoplastically processable" preferably describes the fact that the polymer can be molded at a temperature of 60 to 360° C., preferably 80 to 200° C., more preferably 85 to 150° C.—without decomposing.

In a preferred embodiment, the polymers according to the invention have an melt flow index (MFI) of 0.01 to 70 g/10 min, more preferably 0.1 to 50 g/10 min, especially preferably 0.15 to 30 g/10 min, particularly especially preferably 0.5 to 20 g/10 min or, alternatively, 1.0 to 15 g/10 min.

The melt flow index (also known as the melt flow rate, of MFR) characterizes the flow properties of a thermoplastic. In this application, the MFR is preferably determined pursuant to ISO 1133.

Preferred Embodiments for Preparing the Polymers According to the Invention

A further subject matter of the present invention is a method for preparing a polymer according to the present application, comprising the following steps:
(i) providing monomers according to formulas IIa to IIc,
(Ii) if necessary, providing at least one additional monomer, and
(Iii) polymerizing the monomers by or without adding a polymerization initiator.

The polymerization conditions are preferably selected to ensure that the resulting polymer has the aforementioned glass temperature.

All of the preceding commentary on the polymers according to the invention also preferably applies to the method of the invention. The method described herein below is thus suitable for preparing polymers comprising monomers according to formulas IIa to IIc.

In step i of the present method, monomers according to formulas IIa to IIc are provided in solution, suspension, emulsion or as a mass—preferably in a solution, emulsion or suspension.

In an especially preferred embodiment, the monomers according to formulas IIa to IIc are preferably suspended in an aqueous medium through stirring while adding stabilizers (protective colloids) and/or surfactants.

In an alternatively preferred embodiment, the monomers are dissolved—preferably entirely—in a solvent. In addition, the resulting polymer is preferably dissolved—preferably entirely—in the solvent. The solvent is preferably an organic solvent, more preferably an inert organic solvent. Examples of polar organic solvents are ethanol, isopropanol, acetone, methylethylketone and THF.

In optional step ii of the method according to the invention, at least one further monomer may be provided. This at least one further monomer may preferably be selected from the group consisting of a) alkaline monomers, b) acidic monomers, c) associating monomers or d) standard monomers. With respect to the selection and amounts of the further monomers, reference is made to the preceding commentary.

In step iii of the present method, the monomers are polymerized with or without adding a polymerization initiator, especially preferably via an initiator that forms carbon-centric residues. In a further preferred embodiment, polymerization is performed as a living radical polymerization. Nitroxyl residues and the RAFT method are especially well suited to this. The polymerization initiator is preferably a photoinitiator or a substance suitable for thermally initiated radical polymerization, preferably a substance suitable for thermally initiated radical polymerization.

The initiators described as aforesaid are preferably used.

The antimicrobial polymer according to the invention has been described as aforesaid. It can be present as a homopolymer or copolymer. The antimicrobial polymer may be processed to a polymer blend together with a further polymer (also referred to herein as "blend polymer," or BLEPO for short).

The subject matter of the invention thus also includes an antimicrobial polymer blend containing an antimicrobial polymer obtainable by polymerizing a monomer having a structure according to formula I

A-B-C'-D    (I), wherein
A is a radically polymerizable group of the formula —$CR^{V1}$=$CR^{V2}R^{V3}$, wherein $R^{V1}$, $R^{V2}$ and $R^{V3}$, independently of each other, are hydrogen, methyl, chloride, cyano or ester groups,
B is an aromatic spacer,
C' is an aliphatic spacer of the formula —$CR^{S1}R^{S2}$—, wherein $R^{S1}$ and $R^{S2}$, independently of each other, are hydrogen or methyl, and
D is an amine of the formula —$NR^{A1}R^{A2}$, wherein
$R^{A1}$ is a non-aromatic group with 2 to 7 carbon atoms, and
$R^{A2}$ is hydrogen, methyl or a non-aromatic group with 2 to 7 carbon atoms, wherein
$R^{A1}$ and $R^{A2}$ are connected to each other and form a ring together with the nitrogen, wherein the ring includes 3 to 6 carbon atoms, wherein the ring formed can carry up to 4 methyl groups,
wherein the polymer's glass temperature $T_G$ is preferably 60° C. to 200° C.,
and/or
a copolymer obtainable by reacting at least one monomer of the formula I, wherein groups A, B, C' and D are defined as set out above and at least one further monomer, preferably comprising
a) alkaline monomers and/or
b) acidic monomers and/or
c) associating monomers and/or
d) standard monomers,
wherein the copolymer's glass temperature $T_G$ is preferably 65° C. to 230° C.,
and at least one further polymer (BLEPO).

Preferred Group "A" Embodiments

A is a radically polymerizable group of the formula —$CR^{V1}$=$CR^{V2}R^{V3}$, wherein $R^{V1}$, $R^{V2}$ and $R^{V3}$, independently of each other, are hydrogen, methyl, chloride, cyano or an ester group.

In an especially preferred embodiment, each of $R^{V1}$ or $R^{V2}$ or $R^{V3}$ is selected from a methyl, chloride, cyano or an ester group, as a result of which a doubly substituted vinyl double bond is present.

In a further especially preferred embodiment, each of $R^{V2}$ and $R^{V3}$ are hydrogen and $R^{V1}$ is selected from the group consisting of methyl, cyano, chloride and $COOCH_3$.

In a preferred embodiment, the polymerization of the radically polymerizable A group may be a photochemically initiated radical polymerization.

Photochemically initiated polymerization generally involves the use of a compound that undergoes a photo reaction when it absorbs light, preferably in the range of 300 to 450 nm. This reaction generates the reactive species that reacts with the radically polymerizable group, thereby initiating the polymerization. Examples of photoinitiators are 2,2-dimethoxy-2-phenlyacetophenone (DMPA), 1-hyroxy-cyclohexylphenylketone and 2,4,6-trimethylbenzoyldiphenylphosphinoxide.

In an especially preferred embodiment, the polymerization of the radically polymerizable group may be a thermally initiated radical polymerization with or without an initiator.

The radical polymerization may be initiated purely thermally (without an initiator) or via peroxide initiators, azo-initiators, redox systems or photochemically.

Preferred A group polymerization initiators are described as "preferred initiators" in the following section.

Preferred Group "B" Embodiments

In formula I, B is an aromatic spacer. The aromatic spacer is arranged between the radically polymerizable double bond and the aliphatic spacer.

The aromatic spacer B may be any aromatic group, i.e. any group that adheres to the 4n+2 pi-electron rule, wherein n is 0 or a natural number. The aromatic spacer may contain heteroatoms such as nitrogen, oxygen, sulfur and phosphorus in its aromatic system.

B preferably contains structural elements of the group of phenylenes, naphthylenes, phenanthrenes, antracenes, fluorenes, pyridines, pyrimidines, triazines, chinolines, isochinolines, acridines, imidazoles, pyridazines, pyrazines, carbazolea, indoles, and pyrazoles.

The aromatic spacers may contain additional substituents or functionalized substituents in addition to groups A and C'. The following are examples: alkyl, aryl, ester, ether, hydroxy, cyano, aldehyde, ketone, halogen, organic acid, urea, urethane, amide, imide, amine, nitro and sulfonic acid groups, preferably ester, more preferably methylester, keto and cyano groups, especially cyano groups.

In a preferred embodiment, the aromatic spacer is not further substituted. B is preferably selected from a phenylene, naphthylene, pyridyl or carbazol system, especially preferably from a phenylene or naphthylene system, especially a phenylene system.

Preferred Group "C" Embodiments

In formula I, C' is an aliphatic spacer of the formula —$CR^{S1}R^{S2}$—, wherein $R^{S1}$ and $R^{S2}$, independently, may be hydrogen or methyl.

The aliphatic spacer C' is arranged between the aromatic spacer B and the amine D. It has been found that the use of a substituted or unsubstituted methylene as aliphatic spacer can lead to an improved processability and enhanced antimicrobial effect of the resulting polymer.

Moreover, a single or plurality of spacer C' and the D group bonded to it may be present in substituted form at the aromatic spacer, preferably 1 to 3 times and especially preferably 1 to 2 times. In addition, the position of group C' relative to the polymerizable group A in the aromatic spacer is preferably position-independent. Especially preferably, if two substituents are present, the substitution patterns according to which the groups oppose each other directly or diagonally, e.g. the para position for a phenyl spacer or the 1.4, 2.6 or 1.5 position for a naphthalene spacer.

Preferred Group "D" Embodiments

In a preferred embodiment of formula I, D is an amine of the formula —$NR^{41}R^{42}$, wherein $R^{41}$ is a non-aromatic group with 2 to 7 carbon atoms and $R^{42}$ is hydrogen, methyl or a non-aromatic group with 2 to 7 carbon atoms. Alternatively, $R^{41}$ and $R^{42}$ are connected to each other and form a ring together with the nitrogen, wherein the ring includes 3 to 6 carbon atoms, wherein the ring formed can additionally carry up to 4 methyl groups, In a preferred embodiment, the non-aromatic group $R^{41}$ is preferably a linear, branched or cyclical aliphatic group with 2 to 7 carbon atoms, preferably a branched or cyclical aliphatic group with 3 to 7 carbon atoms, especially preferably a branched aliphatic group with 3 to 7 carbon atoms.

Examples of linear aliphatic groups are ethyl, propyl, butyl, pentyl, hexyl and heptyl, preferably ethyl, propyl and butyl.

The cyclical group may be cyclopropyl, cyclobutyl, cyclopentyl or cyclohexyl, preferably cyclopentyl or cyclohexyl.

In an especially preferred embodiment, $R^{41}$ is a branched aliphatic group with 3 to 7 carbon atoms.

Preferred branched aliphatic $R^{41}$ groups are isopropyl, sec-butyl, iso-butyl, tert-butyl, 2-pentyl(sec-pentyl), 3-pentyl, 2-methylbutyl, 3-methylbutyl(isopentyl), 3-methyl-but-2-yl, 2-methylbut-2-yl, 2,2-dimethylpropyl(neopentyl), 2-methyl-3-pentyl, 3-methyl-3-pentyl, 2,3-dimethylbutyl, 2,2-dimethylbutyl(neohexyl) and 3-ethyl-3-pentyl.

More preferably, $R^{41}$ is isopropyl, sec-butyl, iso-butyl, tert-butyl, 3-methyl-but-2-yl, 2-methylbut-2-yl, 2-methyl-3-pentyl, 3-methyl-3-pentyl, 2,3-dimethylbutyl or 3-ethyl-3-pentyl.

Even more preferably, $R^{41}$ is tert-butyl, 2-methylbut-2-yl, 3-methyl-3-pentyl or 3-ethyl-3-pentyl.

Very particularly preferably, $R^{41}$ is 2-methylbut-2-yl. Very particularly preferably, $R^{41}$ is 3-methyl-3-pentyl. Very particularly preferably, $R^{41}$ is 3-ethyl-3-pentyl. Very particularly preferably, $R^{41}$ is tert-butyl.

In a preferred embodiment, the $R^{42}$ group is hydrogen, methyl or a non-aromatic group with 2 to 7 carbon atoms, preferably hydrogen or methyl, especially preferably hydrogen.

In an alternative embodiment, the $R^{42}$ group is a linear, branched or cyclical aliphatic group with 2 to 7 carbon atoms. Examples of such groups correspond to the $R^{41}$ groups described in the aforesaid.

In a preferred embodiment, $R^{41}$ is a non-aromatic branched group with 3 to 7 carbon atoms and $R^{42}$ is hydrogen, a methyl or a non-aromatic group with 2 to 3 carbon atoms.

In a more preferred embodiment, $R^{41}$ is a non-aromatic branched group with 3 to 7 carbon atoms and $R^{42}$ is hydrogen or a methyl group.

In a very particularly preferred embodiment, $R^{41}$ is a non-aromatic branched group with 3 to 7 carbon atoms and $R^{42}$ is hydrogen.

In a preferred embodiment, $R^{41}$ and $R^{42}$ are connected to each other and form a ring together with the nitrogen, wherein the ring includes 3 to 6 carbon atoms, wherein the ring formed can additionally carry up to 4 methyl groups.

Preferred Combinations of Groups A, B, C' and D

In a preferred embodiment of the present invention, the radically polymerizable group is A —CCN=$CH_2$, —$CCH_3$=$CH_2$, —CCl=$CH_2$, —CH=$CH_2$ or —C(COOCH$_3$)=$CH_2$ and/or the aromatic spacer B includes a phenylene, pyridyl, naphthylene or carbazol system and/or the non-aromatic spacer C' is —$CH_2$—, CHCH$_3$ or C(CH$_3$)$_2$ and the residue $R^{41}$ is—in group D—hydrogen or a branched aliphatic group with 3 to 7 carbon atoms and the residue $R^{42}$ is—in group D—a branched aliphatic group with 3 to 7 carbon atoms and/or $R^{41}$ and $R^{42}$ are connected to each other and, together with the nitrogen form a ring, wherein the ring contains 4 to 6 carbon atoms, wherein the ring formed can carry up to 4 methyl groups.

In an especially preferred embodiment, the antimicrobial polymer in the polymer blend according to the invention is a polymer obtainable by polymerizing monomers of the structural formulas IIa to IIc or mixtures thereof:

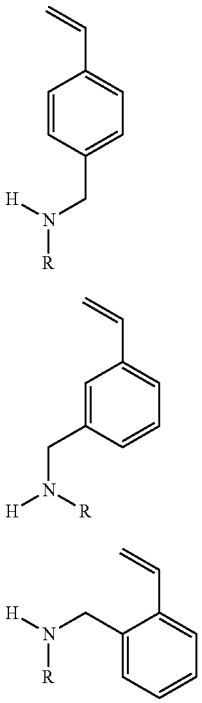

wherein the residue R is defined as described in formulas IIa to IIc as in the aforesaid.

A monomer according to formula IIa is preferred.

In a preferred embodiment of the antimicrobial polymer blend, the antimicrobial polymer is a copolymer obtainable by reacting a monomer according to formula I, wherein groups A, B, C' and D are defined as set out in claim 10 with at least one further monomer, preferably comprising
a) alkaline monomers and/or
b) acidic monomers and/or
c) associating monomers and/or
d) standard monomers,
wherein the copolymer's glass temperature $T_G$ is preferably 65° C. to 230° C.

All of the aforementioned commentary on the a) alkaline monomers, b) acidic monomers, c) associating monomers and d) standard monomers as well as their ranges relative to the total monomer content also preferably apply to the copolymers present in the polymer blend.

Moreover, all of the preceding commentary on the antimicrobial polymers also preferably applies to the antimicrobial polymer blend according to the invention. This particularly applies to the definition of the residues in formulas IIa to IIc as well as to the physical properties such as the antimicrobial properties, thermoplastic processability, water absorption, molecular weight and glass temperature.

Among the preferred polymers (BLEPO) with which the antimicrobial polymer or copolymer may be processed to form a polymer blend in accordance with formula I are: polyvinylpyridine and its copolymers, polyvinylpyrrolidine, polyvinylimidazole, polymethylaminoethylmethacrylates and their copolymers, polyvinylcarbazole and its copolymers, aromatic and aliphatic thermoplastic polyurethane (TPU), polypyrrol, polyacrylic acid (PAA), polymethacrylic acid (PMAA), polymethylmethacrylate (PMMA), MSA-grafted polyethylene (MSA-PE), polychloroacrylic acid, and polycyanoacrylic acid, polyacrylnitrile (PAN), polystyrene-co-acrylonitrile (SAN), polyacrylonitrile butadiene styrene (ABS), polyacrylonitrile butadiene, polyester, polybutylene therephthalate (PBT), polyethylene therephthalate (PET), acrylonitrile butadiene rubber(NBR), styrene butadiene rubber (SBR), methylmethacrylate acrylonitrile butadiene styrene (MABS), various polyamides (PA), e.g. PA 6, PA4/6, PA66, PA6/66, PA66/610, PA11, PA12, PA12/MACMI, polyarylamides, polyethylene vinyl alcohol (EVOH), polyimides, polyvinyl amide, polyacrylamides (PARA), polyvinylbenzonitrile, polyamide imide (PAI), polyether block amides (PEBA), polyimide sulfones (PISU), polyphthalamides (PPA), polyvinylchloride acetate (PVCA), polyetherimide (PEI), polyester amide (PEA), high-impact polystyrene (HIPS), polyolefines, e.g. polyethylenes (PE, LDPE, LLDPE, HDPE, MDPE), polypropylenes (PP), poly(4-methyl-1-pentene) (PMP), ethylene propylene copolymer (EPM), ethylene propylenediene rubber (EPDM), polyoxymethylene (POM), polyvinyichlorides (PVC), polyvinylacatete (PVA), polyethylenvinylacetate (EVA), polyetherketones, polyphenylenether (PPE, PPO), copolymers of ethene and vinylacetete (EVM), polycarbonates (PC), butadiene rubber (BR), ethylene propylene rubber (EPM), polyisoprene (NR, IR), polyethersulfones (PES), polyvinylidene chloride (PVDC), poly(2,6-diphenyl phenylene oxide), TPEs, acrylate butadiene rubbers (ABR), polyarylether (PAE), polyarylsulfones (PASU), poly-a-methylstyrene-co-acrylonitrile (AMSAN), poly-a-methylstyrenes (PAMS), polycyclohexylene dimethylenterephthalate (PCT), polydimethylsiloxane (PDMS), polyetheretherketones (PEEK), polyetherketone etherketone ketones (PEKEKK), polyetherketone ketones (PEKK), polyethylene naphthalates (PEN), polymethacrylmethylimide (PMMI), perfluoralkoxypolymer (PFA), polyperfluoropolyether (PFPE), polytetrafluoroethylen (PTFE), acrylonitrile methylmetacrylate (AMMA), polyvinylchloride ethylene (VCE), polyvinylchloride ethylene methyl acrylate (VCEMA), polyvinylchloride methylacrylate (VCMA), polyvinylchloride vinylidene chloride (VCVDC), acrylonitrile chlorinated polyethylen styrene terpolymer (ACS), acryloester styrene acrylonitrile (ASA), acrylonitrile butadiene acrylate (ABA), cellulose ester (CA, CAB, CP), cellulose nitrate (CN), cycloolefincopolymeres (COC), ethylene acrylate copolymer, polyhydroxyalkanoates (PHA), polyhydroxybutyrates (PHB), polyvinylidene fluoride, methyl cellulose (MC) and mixtures thereof.

Especially preferred are polyvinylpyridine and its copolymers, polyvinylpyrrolidine, polyvinylimidazoles, and their copolymers, polyvinylcarbazole and its copolymers, aromatic and aliphatic thermoplastic polyurethane (TPU), polypyrrole, polyacrylic acid (PAA), polymethacrylic acid (PMAA), polymethylmethacrylate (PMMA), MSA grafted polyethylene (MSA-PE), polychloroacrylic acid, and polycyanoacrylic acid, polyester, polybutylene therephthalate (PBT), polyethylene therephthalate (PET), various polyamides (PA) e.g. (PA 6, PA4/6, PA66, PA6/66, PA66/610, PA66, PA 12,), Polyarylamide, Polyimide, polyacrylamides (PARA), polyamideimide (PAI), polyether block amides (PEBA), polyphthalamides (PPA), polyesteramide (PEA), polyoxymethylene (POM), polyetherketones, polyphenylene ether (PPE, PPO), polyamides, polycarbonates (PC), polyethersulfones, poly(2,6-diphenyl phenylene oxide), polyarylether (PAE), polyarylsulfones (PASU), polycyclohexylene dimethylenterephthalate (PCT), polyethersulfones (PES), high-impact polystyrene (HIPS), polyolefines such as polyethylene (LDPE, LLDPE, HDPE, MDPE) polypropylenes (PP), ethylene propylene copolymer (EPM), ethylene propylene diene rubber (EPDM), polyoxymethylene (POM), polyvinylchlorides (PVC), polyvinylacetate (PVA), polyethylene vinylacetate (EVA), acrylonitrile styrene copolymer (SAN), acrylonitrile butadiene styrene (ABS), acrylic ester styrene acrylonitrile (ASA), acrylonitrile butadiene acrylate (ABA) and mixtures thereof.

Even more preferred are polyolefins, especially PE and PP.

Examples of preferred polyolefins are polyethylenes, e.g. high-density polyethylene (HDPE, density higher than 0.944 g/cm$^3$ to max. 1.2 g/cm$^3$), medium-density polyethylene (MDPE, density of 0.926 to 0.940 g/cm$^3$), linear medium-density polyethylene (LMDPE, density of 0.926 to 0.940 g/cm$^3$), low-density polyethylene (LDPE, density of 0.910 to 0.925 g/cm$^3$) and linear low-density polyethylene (LLDPE, density of 0.916 to 0.925 g/cm$^3$), or mixtures thereof, polypropylenes, amorphous or crystalline polypropylene, atactic or isotactic polypropylene or mixtures of said polypropylenes, axialyl or biaxially oriented polypropylene or cast polypropylene, poly-1-butene, poly-3-methylbutene, poly-4-methylpentene and copolymers thereof, e.g. of polyethylene with vinylacetate, vinylalcohol, acrylic acid, e.g. ionomer resins such as copolymerisates of ethylene with approximately 11% acrylic acid, methacrylic acid, acrylic esters, tetrafluoroethylene or polypropylene as well as statistic copolymers, block copolymers or olefinpolymer-elastomer mixtures. Alternatively preferred are ABS, polyamides and PS. Further alternatively preferred is thermoplastic polyurethane (TPU).

In a preferred embodiment, the polymer blend according to the invention contains 1 to 99 mol %, preferably 5 to 95 mol %, more preferably 10 to 90 mol %, even more preferably 15 to 85 mol %, particularly 30 to 80 mol % of the homopolymer of the invention according to formula I or formulas IIa to IIc and 1 to 99 mol %, preferably 5 to 95 mol %, more preferably 10 to 90 mol %, even more preferably 15 to 85 mol %, particularly 20 to 70 mol % of the further polymer (BLEPO) or any mixtures of said polymers.

In an alternatively preferred embodiment, the polymer blend of the invention contains 1 to 40 mol %, preferably 3 to 35 mol %, more preferably 5 to 30 mol %, even more preferably 7 to 25 mol %, particularly 8 to 30 mol % antimicrobial polymer according to formula I and 30 to 90 mol %, preferably 40 to 85 mol %, more preferably 45 to 80 mol % of a further polymer (BLEPO).

In an alternatively preferred embodiment, the polymer blend of the invention contains 1 to 40 wt. %, preferably 3 to 35 wt. %, more preferably 5 to 30 wt. %, even more preferably 7 to 25 wt. %, particularly 8 to 30 wt. % antimicrobial polymer according to formula I or formula IIa to IIc and 30 to 90 wt. %, preferably 40 to 85 wt. %, more preferably 45 to 80 wt. % of the further polymer (BLEPO).

In the event that a small amount of the polymer blend of the invention is applied to the article that is to be treated antimicrobially, for instance as a film, the polymer blend usually contains 3 to 99 wt. %, preferably 5 to 95 wt. %, particularly 8 to 80 wt. % antimicrobial polymer according to formula I or formulas IIa to IIc and 1 to 60 wt. %, preferably 2 to 30 wt. %, more preferably 5 to 10 wt. % of the further polymer (BLEPO). In a preferred embodiment, the film has a thickness of 1 nm to 100 µm. In an alternative embodiment, if the film is applied, e.g. via extrusion, it has a thickness of 1 to 100 µm, preferably 1 to 50 µm, more preferably 1 to 20 µm. In a further alternative embodiment, if the film is applied, e.g. via printing or lacquering, it has a thickness of 1 nm to 15 µm, preferably 5 nm to 1 µm, more preferably 5 to 500 nm.

In a preferred embodiment, the polymer blend according to the invention contains 1 to 99 mol %, preferably 30 to 95 mol %, more preferably 50 to 90 mol % of the copolymer of the invention and 1 to 99 mol %, preferably 5 to 70 mol-%, more preferably 10 to 50 mol % of the further polymer or any mixtures thereof.

In an alternatively preferred embodiment, the polymer blend of the invention contains 1 to 40 mol %, preferably 3 to 35 mol %, more preferably 5 to 30 mol %, even more preferably 7 to 25 mol %, particularly 8 to 30 mol % antimicrobial copolymer and 30 to 90 mol %, preferably 40 to 85 mol %, more preferably 45 to 80 mol % of a further polymer (BLEPO).

In an alternatively preferred embodiment, the polymer blend of the invention contains 1 to 40 wt. %, preferably 3 to 35 wt. %, more preferably 5 to 30 wt. %, even more preferably 7 to 25 wt. %, particularly 8 to 30 wt. % antimicrobial copolymer and 30 to 90 wt. %, preferably 40 to 85 wt. %, more preferably 45 to 80 wt. % of the further polymer (BLEPO).

The antimicrobial polymer and the at least one further polymer (BLEPO) is preferably present as a single or multi-phase mixture in a polymer blend, wherein a compatibilizer is used.

As described in the aforesaid, the blends may be processed thermoplastically.

Preferred Embodiments of Optional Additives

In a preferred embodiment, both the antimicrobial homopolymer and/or the copolymer (as well as the antimicrobial polymer blend of the invention) preferably include additives common in polymer chemistry. Examples of additives include fillers, adhesion promoters, plasticizers, stabilizers such as antioxidants, light stabilizers and flame retardants, uv absorbers, quenchers, impact strength enhancers, reinforcers (beads, fibers, etc.), antistatic agents, metal deactivators, anti-fog additives, colorants, lubricants, propellants, mold separating agents and processing auxiliaries.

Fillers are generally used as functional additives or extenders. Examples of fillers are titanium oxide, aluminum hydroxide, silicon oxide, aluminum silicates, calcium carbonate, calcium sulfate, barium sulfate, tungsten oxide, chromium oxide, vanadium oxide, molybdenum oxide, talcum, carbon black and starch. Fillers may be present in an amount of 0 to 80 wt. %, preferably 5 to 30 wt, % relative to the total weight of the polymer according to the invention or of the polymer blend according to the invention.

Adhesion Promoters

In a preferred embodiment, the blend according to the invention contains the antimicrobial polymer and the further polymer (BLEPO) as well as adhesion promoters (as described herein below). The adhesion promoter is preferably added during compounding.

Adhesion promoters preferably have reactive groups and can react with the antimicrobial polymer. This keeps the antimicrobial polymer from migrating from the blend and/or bonding to another polymer layer. Examples of adhesion promoters are grafted polymers such as grafted LDPE, grafted LLDPE, grafted HDPE and grafted polypropylene. The polymers are preferably grafted with laleic acid anhydride. Moreover, the adhesion promoter between the plastic films and carrier materials may be vinylchloride copolymerisates, polymerizable polyester, vinylpyridine polymerisates, vinylpyridine polymerisates in combination with epoxy resins, butadiene arylonitrile methacrylic acid copolymerisates, phenolic resins, rubber derivates, acrylic resins, acrylic resins with phenol or epoxy resins, silicon organic compounds such as organosilanes, modified polyolefines such as acid-modified polyolefines or ethylene acrylic acid (EAA). EAA (ethylene acrylic acid) or modified polyolefines, e.g. modified polypropylene, are preferred. One preferred modified polypropylene is an adduct of maleic acid anhydride and an ethylene propylene copolymer. Very particularly preferred are dispersions of modified polyolefins. An example of a dispersion of a modified polypropylene is Morprime (brand name of Morton International of Norton Norwich Products, Inc.). Further suitable adhesion promoters are adhesives such as nitrile rubber phenol resins, epoxides, acrylonitrile butadiene rubber, urethane-modified acryls, polyester co-polyamides, hot melt polyesters with hot melt polyester-crosslinked polyisocyanates, polyisobutylene-modified styrene butadiene rubbers, urethanes, ethylene acrylic acid blend polymers and ethylenevinylacetate blend polymers. Adhesive promoters may be used, e.g. in an amount of 0.01 to 25 wt. %, preferably 0.5 to bis 5 wt. %. The adhesive promoters are usually applied with a thickness of 1 to 10 µm.

Adhesives

"Adhesives" is the term commonly used to designate substances/mixtures of substances that are suitable for gluing various materials to each other. Adhesives may preferably have a reactive system. In the event that the adhesives used are, for example, laminating adhesives, the laminating adhesives may or may not contain solvents and may contain water. Examples are solvent-containing, solvent-free or aqueous acrylate adhesives or polyurethane adhesives (1 or 2-component PU adhesives) or epoxy resin adhesives.

The aqueous dispersion adhesives used may be dispersion adhesives. These may be based on the binders commonly used in adhesives such as polycondensates, copolymerisates and polyaddition products, as long as they can be processed as an aqueous composition. Examples of compounds of this kind are acrylic and methacrylic acid ester polymerisates; copolymers of ethylenically unsaturated compounds such as ethylene, propylene, styrene, vinylacetate, vinylidene chloride, maleic acid anhydride and esters of maleic acid, polyesters and polyurethanes. The adhesives used are preferably based on OH functional polyurethanes or poly(meth) acrylates. The aqueous disperisons may be solvent-free or contain small amounts of common organic solvents. Aqueous dispersions that are free of organic solvents are preferred. Adhesives may be used, e.g. in an amount of 0.01 to 25 wt. %, preferably 0.5 to 5 wt. %. The adhesives are preferably applied with a thickness of 0.05 to 10 µm.

Plasticizers

Plasticizers are substances that reduce the brittleness and hardness of plastics. Examples of plasticizers are semi-volatile esters (such as aliphatic di or polycarboxylic acid esters, esters of pentaerythrite or dipentaerythrite, or polyesters of adipic, sebacic and azelaic acid having a molecular weight of 550 to 3,500 g/mol), fatty oils, soft resins, sulfonamides or camphor. Plasticizers may be present in an amount of 0 to 40 wt. %, preferably 0.1 to 25 wt. %, more preferably 0.5 to 15 wt. % relative to the total weight of the polymer according to the invention or of the polymer blend according to the invention.

The stabilizers serve to improve the chemical properties and protect the plastic against oxidation, strong (light) radiation and fire. Stabilizers may be present in an amount of 0 to 25 wt. %, preferably 0.1 to 15 wt. % relative to the total weight of the polymer according to the invention or of the polymer blend according to the invention.

The antioxidants are substances that capture free radicals, reduce hydroperoxides and thereby prevent the plastic from decomposing (molar mass decomposition, discoloration and cracking). Examples of antioxidants are alkylates, phenoles, amines (HALS and HAS) and phosphates. Antioxidants may be present in an amount of 0 to 20 wt. %, preferably 0.1 to 10 wt. % relative to the total weight of the polymer according to the invention or of the polymer blend according to the invention.

Light stabilizers protect plastic against damage from strong light radiation, in particular high-energy UV light. Light stabilizers that may be used are, e.g. carbon black, o-hydroxybenzenephenones, hydroxybenzotriazoles, cinnamic acid derivatives and dialkyl dithiocarbamates. Light stabilizers may be present in an amount of 0 to 20 wt. %, preferably 0.1 to 5 wt. % relative to the total weight of the polymer according to the invention or of the polymer blend according to the invention.

Quenchers absorb the radiation energy absorbed by chromophores and pass it on as heat or fluorescence or phosphorescence radiation, thereby protecting the polymer against high-energy UV radiation. Quenchers may be present in an amount of 0 to 15 wt. %, preferably 0.1 to 3 wt. % relative to the total weight of the polymer according to the invention or of the polymer blend according to the invention.

Flame retardants either prevent oxygen from reaching the fire site or the chemical reactions (radical chain reactions) that occur during combustion. Examples of flame retardants are aluminum hydroxide, polybrominated substances in connection with antimony oxide as well as phosphor-containing compounds, ammonium polyphosphates and boron compounds. Flame retardants may be present in an amount of 0 to 70 wt. %, preferably 0.1 to 30 wt. % relative to the total weight of the polymer according to the invention or of the polymer blend according to the invention.

Reinforcing materials are organic or inorganic substances that strengthen the plastic matrix and improve both mechanical and physical properties. Examples of two-dimensional reinforcing materials are roving, fabrics, wovens and knitted goods as well as cut fibers. Examples of fibrous reinforcing materials are carbon, aramid, glass, polyester and flax. Examples of particulate reinforcing materials are talcum as well as mica and glass beads. Reinforcing materials may be present in an amount of 0 to 50 wt. %, preferably 1 to 35 wt. % relative to the total weight of the polymer according to the invention or of the polymer blend according to the invention.

Anti-static agents are substances that weaken or prevent plastics from being charged electrically. Examples of anti-static agents are quaternary ammonium compounds. Anti-static agents may be present in an amount of 0 to 20 wt. %, preferably 0.1 to 5 wt. % relative to the total weight of the polymer according to the invention or of the polymer blend according to the invention.

Lubricants and processing auxiliaries prevent deposits from being formed on hot steel surfaces and improve the rheological behavior of the polymer melt. This is achieved, inter alia, by preventing build-up from forming on the steel surfaces, because a wall-slipping plug flow ensues.

Colorants impart color to the colorless plastic. Colorants break down into dyes and pigments. Colorants may be present in an amount of 0 to 20 wt. %, preferably 0.01 to 10 wt. % relative to the total weight of the polymer according to the invention or of the polymer blend according to the invention.

Mold-release agents are surface-active substances that facilitate or enable demolding from the tool. Mold-release agents may be present in an amount of 0 to 10 wt. %, preferably 0.5 to 5 wt. % relative to the total weight of the polymer according to the invention or of the polymer blend according to the invention.

Propellants are organic or inorganic substances that enable the production of foamed plastic articles. They decompose as gases form during thermoplastic processing, thereby creating a foam structure in the polymer matrix. Propellants may be added before or during thermoplastic processing in an amount of 0 to 20 wt. %, preferably 0.1 to 8 wt. % relative to the total weight of the polymer according to the invention or of the polymer blend according to the invention.

In a preferred embodiment, the polymers according to the invention or the polymer blend according to the invention contain compounds having one or several acid groups or acid anhydride groups.

The acid group-containing compounds are preferably compounds containing carboxylic acid, sulfonic acid, and phosphinic acid groups.

Examples are alkene di-acids and their anhydrides such as glutaric acid, succinic acid, adipinic acid, dodecane di-acid, cyclohexane dicarboxylic acid, alkyl malonic acid, maleic acid, fumaric acid, malic acid, tartaric acid and citric acid. Examples of anhydrides and substituted anhydrides are glutaric acid anhydride, succinic acid anhydride, alkyl succinic acid anhydride such as dodecyl succinic acid anhydride, maleic acid anhydride, etc. Further examples are aromatic di-acids such as phthalic acid, terephthalic acid, benzene disulfonic acid, polyphosphoric acid, etc. and mixtures thereof as well as polyesters of these acids, which have acid groups as end groups or in their chain. Examples of poly-acids are polyacrylic acids, polymethacrylic acid (PMAA), polychloroacrylic acid, polycyanoacrylic acid, polyphosphoric acid, polyvinylphosphonic acid and polyvinylsulfonic acid. Examples of polyanhydrides include MSA-grafted polyethylene (MSA-PE).

Preferred compounds are those that have one or more acid groups or acid anhydride groups in an amount of 0 to 60 wt. %, more preferably 0.1 to 30 wt. %, even more preferably 0.5 to 15 wt. % and particularly preferably 1.0 to 10 wt. %, relative to the total weight of the polymer according to the invention or of the polymer blend according to the invention.

The aforementioned compounds (additives) may be added to the polymers of the invention during or after polymerization.

Alternatively, the aforementioned compounds (additives) may be added to the polymer blend of the invention during and after compounding the polymer components.

The subject matter of the present application also comprises the use of a polymer obtainable by polymerizing a monomer having the structure of formula I $$A\text{-}B\text{-}C'\text{-}D \qquad (I),$$

wherein groups A, B, C' and D are defined as in the aforesaid,
wherein the polymer's glass temperature $T_G$ is preferably 60° C. to 200° C.,
and/or
a copolymer as described in the aforesaid,
and/or of a polymer blend as described in the aforesaid for the antimicrobial treatment, for the production of antimicrobial products or for the production of antimicrobial composite elements, wherein the polymer (i.e. the homopolymer or copolymer) or the polymer blend can preferably be processed thermoplastically. The use according to the invention thus comprises thermoplastic methods and the methods of applying the polymers and polymer blends of the invention to substrates by printing, immersion, sintering, spraying, concealing, laminating and gluing (e.g. by heating the polymer and pressing it against the carrier) and/or lacquering, e.g. by applying a solution, emulsion or suspension, as described herein below.

All of the preceding commentary on the antimicrobial polymers also preferably applies to the antimicrobial polymer blend according to the invention. This applies in particular to the definition of residues A, B, C' and D as well as to the definition of the a) alkaline monomers, b) acidic monomers, c) associating monomers and/or d) standard monomers.

This enables surfaces of articles to be treated with an antimicrobial polymer or polymer blend in accordance with the invention. In particular, the antimicrobial polymers and polymer blends according to the invention may be used as a coating or superficial layer, for example from the melt, e.g. through extrusion or coextrusion. The term "superficial layer" also comprises components that are made solely of the antimicrobial polymer or polymer blend of the invention, i.e. that consist of them.

Moreover, the antimicrobial polymers and/or polymer blends of the invention may be used for antimicrobial treatment (wherein the polymers/polymer blends as such are processable thermoplastically) wherein they are applied to substrates through dipping, sintering, spraying and/or lacquering, e.g. from a solution or suspension.

If the antimicrobial polymers or blends of the invention are used as a coating, the thickness of the coating is in principle not limited. In a preferred embodiment, the coating has a thickness of 1 nm to 1 cm, preferably of 10 nm to 100 μm. In an alternative embodiment, if the coating is applied, e.g. via extrusion, it has a thickness of 1 to 100 μm, preferably 1 to 50 μm, more preferably 1 to 20 μm. In a further alternative embodiment, if the coating is applied, e.g. via a printing or lacquering process, it has a thickness of 1 nm to 15 μm, preferably 5 nm to 1 μm, more preferably 5 to 500 nm.

The polymer according to the invention can thus still be applied to a carrier (preferably a film) e.g. through a printing process. Printing processes are, for example, flexo printing, screen printing and gravure printing. When a printing process is applied, the polymer of the invention is preferably suspended or dissolved in a solvent and applied from it, for example as a lacquer. Usable solvents are organic solvents, for example ethylacetate.

Furthermore, the polymers and/or polymer blends of the invention may be applied to films or other articles via doctoring or rolling.

Moreover, the polymers and polymer blends of the invention may be applied to metallic and conductive surfaces cataphoretically in neutralized or partially neutralized state.

In addition, the antimicrobial polymers and/or polymer blends of the invention may also be used as additives and components for formulating polymer blends, paints, lacquers and biocides.

The polymers and/or polymer blends of the invention may be processed especially advantageously through extrusion, injection molding, printing, calendering as well as through coextrusion with further polymers.

The subject matter of the present invention also includes the use of the antimicrobial polymers and/or polymer blends of the invention for the production of antimicrobially effective products.

Such products may be produced from the antimicrobial polymers or polymer blends of the invention or are based on combinations of the antimicrobial and polymer blends and carrier materials. If the antimicrobial polymers or polymer blends are applied to a carrier material, they are referred to as composite elements. Therefore, the composite elements preferably comprise a carrier material and a coating containing the antimicrobial polymer of the invention or the polymer blend of the invention. The coating preferably has the aforementioned thickness. In a preferred embodiment, adhesive promoters and/or adhesives may be present between the layers of a composite element. The aforesaid generally applies to adhesive promoters and adhesives. The adhesive promoters are preferably applied with a thickness of 1 to 10 µm.

Examples of carrier materials are polystyrene, polyacrylonitrile, polystyrene-co-acrylonitrile (SAN), polymetylmethacrylate (PMMA), polyacryl nitrile butadienestyrene (ABS), aliphatic and aromatic thermoplastic polyurethane (TPU), polyurethane (flexible foams, semi-rigid foams, rigid foams, elastomeres, coatings, casting compounds, integral foams, etc.), polyester, polyacrylates, polybutylene terephthalate (PBT), polyethylene terephthalate (PET), polycarbonate (PC), polyvinyl chloride (PVC), acrylonitrile butadiene acrylate (ABAK), acrylate butadiene rubber (ABR), polyvinyl acetate (PVA), copolymers of ethene and vinylacetate (EVM), TPE, ethylenevinylacetate and PVC (EVAPVDC), MSA-grafted polyethylene (MSA-PE), methylmethacrylate acrylonitrile butadiene styrene (MABS), polyvinylidene chloride (PVDC), polyphenylene ether (PPE), poly(2,6-diphenyl-phenylene oxide) (PPO), polyarylamide, polyethylene vinylacetate (EVA), polyethylene vinyl alcohol (EVOH), polyoxymethylene (POM), ethylene propylene terpolymer (EPDM), butadiene rubber (BR), polyisoprene, acrylonitrile butadiene rubber (NBR), styrene butadiene rubber (SBR), ethylene propylene rubber (EPM) and mixtures thereof, polyvinylpyridine and its copolymers, polyvinylpyrrolidine, polyvinylimidazoles, polyalkylaminoethylmethacrylates and their copolymers, polyvinylcarbazoles and their copolymers, polypyrrol, polyacrylic acid (PAA), polymethacrylic acid (PMAA), polychloride acrylic acid, polycyanoacrylic acid, alkaline aliphatic polyurethane (ATPU), polyacrylic nitrile butadiene, acrylonitrile butadiene acrylate (ABAK), methylmethacrylate acrylonitrile butadiene styrene (MABS), various polyamides (PA) z.B. (PA 6, PA46, PA66, PA6/66, PA66/610, PA610, PA12, PA12/MACMI, PA6/6T, PA6/12, etc.), polyarylamides, polyimides, polyvinylamide, polyacrylamides (PARA), polyvinyl benzene nitrile, polyamide imide (PAI), polyether block amides (PEBA), polyimide sulfones (PISU), polyphthalamides (PPA), polyvinylchloride acetate (PVCA), polyetherimide (PEI), polyesteramide (PEA), high-Impact polystyrene (HIPS), polyolefines (e. g. polyethylenes and polypropylenes), poly(4-methyl-1-pentene) (PMP), ethylene propylene copolymer (EPM), ethylene propylene diene rubber (EPDM), polyetherketones, acrylate butadiene rubbers (ABR), polyarylether (PAE), polyarylsulfones (PASU), poly-a-methylstyrenes (PAMS), polycyclohexylene dimethylene terephthalate (PCT), polydimethylsiloxane (PDMS), polyetheretherketones (PEEK), polyether ketone ether ketone ketones (PEKEKK), polyether ketone ketones (PEKK), polyethylene naphthalate (PEN), polyether sulfones (PES), polymethacrylic methyl imide (PMMI), perfluoroalkoxypolymer (PFA), polyperfluoropolyether (PFPE), polytetrafluoroethylene (PTFE), acrylonitrile methylmethacrylate (AMMA), polyvinyl chloride ethylene (VCE), polyvinyl chloride ethylene methyl acrylate (VCEMA), polyvinyl chloride methyl acrylate (VCMA), polyvinylchloride vinylidene chloride (VCVDC), acrylonitrile chlorinated polyethylene styrene terpolymer (ACS), acrylonitrile butadiene acrylate (ABA), cellulose acetate (CA), cellulose nitrate (CN), cyclo olefin copolymers (COC), ethylene ethylacrylate copolymer (E/EA), polyhydroxyalkanoates (PHA), polyhydroxybutyrates (PHB), polyvinylidene fluoride, methyl cellulose (MC), and mixtures thereof as well as carrier materials made of metal, semi-metals, wood, paper, carton, glass, ceramics and mixtures of said carriers. In an alternative embodiment, the carrier material may be a sheet with a thickness of 60 µm bis 6 mm. The sheet may contain metal such as steel or aluminum or consist thereof.

The subject matter of the invention is thus a composite element containing carrier material, preferably selected from the aforementioned carrier materials, and antimicrobial polymer of the invention as well as—optionally—adhesive promoters. Alternatively, a product or component may be made solely of the antimicrobial polymer or polymer blend. The subject matter of the invention is thus a product or component comprising or consisting of the antimicrobial polymer or polymer blend of the invention.

The following are examples of antimicrobial products and composite elements according to the invention:

Antimicrobial plastic packagings for cosmetic and sanitary products, medical articles, medicaments and artificial food as well as packagings for food or the feed sector such as films, multilayer films, bowls, MAP packagings, tumblers, bottles, sealed trays, tubes, single-use trays and glasses, bottles, Tetra Paks, cooling bags, coffee bags, multilayer packagings made of various materials, caps, fasteners, pouring systems, ice packagings, etc.

Antimicrobial components such as food transport boxes, truck superstructures, container claddings, food warehouse and warehousing system equipment, linings for transportation systems, drinking water containers, applications in the fields of slaughtering and slaughterhouses, beverage bottling, products used in cattle farming, products used to bottle and produce, e.g. medicaments, beverages, cosmetics, food, etc.) machine parts and conveyor systems, drinking water systems as well as components used in water systems, water filters, ion exchangers, refrigerators and freezers as well as linings of cooling lubricant tanks and containers Antimicrobial components for air conditioning applications such as air-conditioning systems and air filters, etc Kitchenware components, kitchen surfaces, cutting boards, further kitchen articles, etc.

Semi-finished products, roofings, toys, plastic components and coatings used in swimming pools, etc.

Plastic components used in pubic transportation, in saunas and bathrooms and in transportation systems (airplanes, buses, patient transportation, trains of all kinds, taxis and ships)

Water transportation and shower system components, filter systems, process water, solar panels, heat exchangers, membranes, etc.

Sanitary installation components, wastewater transportation systems and installations in public restrooms, toilet seats, bathroom articles, etc.

Consumables such as toothbrushes, combs, sponges, cleaning cloths for use in kitchens and households, shower curtains, toilet articles, etc.

Plastic components used in furniture, interior decoration and equipment as well as their surfaces in hospitals, medical and dental practices, in particular in rooms in which medical intervention takes places and in quarantine stations for patients with dangerous infections, in nursing wards, in particular in the fields of intensive care and infant care, in veterinary practices and institutions (e.g. floors, door handles and hand holds, light switches as well as chair and deckchair covers) etc.

Consumables for use in medical and nursing applications such as packagings for sterile medical instruments, catheters, infusion bags, tubes, membranes, implants, protective sheets, surgical instruments, disposable gloves, diapers, hospital shoes and clothing, dressings, band-aids, blood bags, drainages, guide wires and surgical instruments, films for touch panels and various devices used in the medical and nursing fields, etc.

Medical engineering products, e.g. contact lenses, membranes and implants

Functional clothing for hygienic applications (e.g. in hospitals, slaughtering operations or in food processing) etc.

Plastic components used in rehabilitation, stretchers, prostheses, exercise and sporting equipment, decubitus bedding layers and cushions, mattress covers, wheelchairs, incontinence toppers, etc.

Emergency care systems (water processing installations, water storage, beverage containers, food storage systems, mobile hospitals and components for use in this field, consumables, stretcher and hospital bed toppers, for rapid medical and sanitary care, etc.) used in natural disasters, war deployments, etc.

Products used in laboratories in the medical sector as well in life sciences and industry such as plugs and sterile plugs, caps, separating instruments, innoculation loops and vaccination needles, spatulas, storage containers, tubes, protective gear, disposable test tubes, dishes, membranes, pipette tips, sealing films, microscope slides, test tubes/centrifuge tubes, tapes, adhesive tapes, disposable gloves, pipettes, disinfecting accessories, disinfecting wipes, pistons, screw caps, dispensers, hand dispensers, dosing systems, filters, syringe filter holders, dialysis tubes and dialysis systems, medical devices and components for medical devices, filter paper, sterile filtration, bag connections, embedding cassettes and sealing films, etc.

Animal and pet husbandry equipment, e.g. feeding bowls, litter boxes, baskets, stable equipment components, e.g. feed transportation systems, troughs and feed dosing systems, water dosing systems, stall finishings, ventilation systems, animal cage and house components, etc.

Films for biogas systems, bioreactors, silage films, agricultural films, arpaulins, textiles, wallpaper, etc.

Sealant material, e.g. joint seals, sealing compounds, flat seals, multilayer seals, fiber-reinforced seals, molded seals, profile seals, etc.

Single and multilayer cable sheaths

Structural and housing materials used, e.g. in electronic devices, operating elements (touch panels, keyboards and computer mice), cellphones, surfaces of doors, carpets, wallpaper, port installations, buoys, drilling rigs, ballast water tanks, basements, walls, facades, etc.

Container, tank and filter mat liners (food, oil and heating oil, medicaments and water) etc.

In paints and coatings and to line paint and coating containers, to clad insulation systems and facades, etc.

A further preferred subject matter are films containing the antimicrobial polymer or the antimicrobial polymer blend according to the invention.

A film is understood to be a thin, two-dimensional material. Moreover, films may have varying degrees of flexibility, with the flexibility being significantly dependent on the thickness of the film as well as on the type of raw material used. Once a certain degree of rigidity/brittleness has been reached, one begins to speak of a plate instead of a film.

The thickness of the films according to the invention is preferably between 1 and 500 µm. Films with a small thickness are often referred to as membranes.

Moreover, the films according to the invention may be transparent or opaque, preferably transparent.

In a preferred embodiment, the film according to the invention may be a monolayer film. The monolayer film consists of a layer of uniform material.

In an alternative, more preferred embodiment, the film according to the invention may be a multilayer film or a composite film, i.e. the film according to the invention includes more than one layer and may comprise various materials. Examples of these materials are plastics commonly used to manufacture films such as polyolefins, halogenated polyolefins, thermoplastic polyurethane, polyamides, EVOH (ethylene vinyl alcohol copolymer), polyester and polycarbonate.

Thermoplastic processing is clearly the most important method of manufacturing plastic films. This is done via calendering or extruding. Depending on tooling, one distinguishes between the blown film and the flat film method. Extrusion and coextrusion are also of major significance in the manufacture of films.

The casting method involves reshaping organic polymers from solutions. It is employed when the materials involved do not melt or only melt if they decompose. Examples are cellulose and polyimides. Since solvents are required to carry out the casting method and have to be recycled, it is less environmentally friendly than thermoplastic reshaping. In specific cases—particularly when manufacturing very thin films such as polycarbonate films—casting methods are also applied to thermoplastics. Sintering methods are limited to special products such as tetrafluoroethylene films and polyimide films.

Furthermore, multilayer films include plastic films as well as metal films such as aluminum films.

The multilayer films according to the invention are preferably thermoplastic films consisting of one or more bonded layers, which may differ from one another or be similar to each other and can be used to manufacture flexible packagings. The film layers are commonly extruded or laminated. This composite film is made up of various layers, which are specified to suit the application in question. The film layers are bonded to form a composite through solvent-free or solvent-containing lamination, i.e. adhesive lamination. Further production methods employed include extrusion lamination, extrusion coating and coextrusion. Composite films that are not manufactured in a single step as in coextrusion are obtained through further film processing. To this end, various technological processes such as cutting and wrapping are employed in order to attain the desired functionality.

Further film processing methods change the film surface via vapor phase deposition, coating, printing or flock coating, wherein the surface treatment is mostly integrated in film production. Of course, this may also apply to simple process chains, e.g. as a result of switching on a printing mechanism in a film production process. Film processing also includes the manufacture of pouches, bags, tote bags, recyclable transport containers and other molded plastic parts which are intended to come into contact with food. Examples of this are plastic films, multilayer films and film pouches, composite films for food packagings;

primary packagings that come into contact with food directly such as PET bottles, beakers, plastic closures for packagings;

plastic bags and pouches that are intended to come into contact with unpackaged food;

food processing machine parts and plants that come into direct contact with food, containers;

crockery, cutlery, kitchen utensils of all types, storage containers, kitchen device parts that come into direct contact with food (all of which are made of plastic);

sealants and sealing inserts in closures.

Composite films can be designed in order to combine the properties of the individual layers to form a property profile that is optimally adapted to the intended use. The use of the polymer or polymer blend of the invention in a composite film thus results in an antimicrobial property.

For instance, the films according to the invention are especially preferably used in composite films for meat and meat product packagings, firm sterilizable packagings or for medical packagings.

As described in the aforesaid, the composite film according to the invention consisting of at least one layer of the polymer or copolymer of the invention with at least one further layer may be produced via extrusion, preferably coextrusion, extrusion coating or extrusion lamination. A flat film extrusion method is particularly preferred in this regard. The composite film according to the invention may be produced from the at least two aforementioned layers also with the assistance of adhesive promoters or laminating adhesives together with the remaining layer sequence of the composite film of the invention that is separately manufactured via extrusion, preferably coextrusion. Moreover, the multilayer film according to the invention may be combined with further substrates made of paper such as Pergamon paper, fabric and/or metal.

By thermoforming—preferably deep drawing—the multilayer film, corresponding packaging containers, preferably packaging vats, may be produced, which are closed by sealing using the usual, preferably transparent, hot-sealable multilayer films, which preferably have a water vapor barrier layer.

The packagings according to the invention, of which at least one packaging element comprises a packaging material of the composite film according to the invention made of the aforementioned at least two layers, are always characterized in that the layer containing the antimicrobial polymer or polymer blend faces the packaged good as a surface layer.

The subject matter of the present invention thus also includes a packaging having at least one packaging element made of a packaging material comprising the composite film of the invention made of the at least two films, wherein the total packaging consists of the multilayer film according to the invention.

The subject matter of the present invention thus also includes a packaging, the packaging recess and preferably the second packaging element of which also consist of the multilayer film according to the invention, acting as a cover film.

The subject matter of the invention also includes packaging bags manufactured from the multilayer film according to the invention.

Moreover, the antimicrobial polymers and polymer blends of the invention may be used to produce fibers or to coat fibers.

These fibers may be obtained through known production and processing methods.

These include various spinning methods such as wet spinning, dry spinning, gel spinning, melt spinning and dispersion spinning.

Melt spinning produces antimicrobial fibers for example by heating the antimicrobial polymer or copolymer of the invention or a mixture of the antimicrobial polymer with a further polymer (BLEPO) after which this is pressed through nozzles, e.g. using a spinning pump. The fibers may have a thickness of 1 µm to 1 mm, preferably 2 µm to 1 mm, more preferably 5 to 500 µm. The fibers obtained are then preferably processed further. To this end, they are for example pulled off, stretched and left to cool. The antimicrobial polymer is thus preferably present in the fiber matrix in fixed state.

The antimicrobial fibers may also be obtained as a result of using fibers made of antimicrobial polymer/copolymer with fibers made of microbiologically neutral polymers with each other in a spinning process. On principle, the following microbiologically neutral polymers may be used: silk, artificial silk, cotton, wool, flax, ramie, aramide, polyamide, polyester, polyacryl derivatives, polyethylene, polypropylene, PTFE, polymethacrylates, polysulfones, polyacrylonitriles, cellulose, cellulose acetate, cellulose derivates or mixtures thereof. These polymers may be used as a basic fiber for coating, as a blend component or as a further fiber in a blended fabric.

The subject matter of the present invention also includes the use of the antimicrobial polymers/polymer blends of the invention for the production of antimicrobially effective products based on said fibers. The fibers according to the invention may, for example, be used to produce:

nonwovens, rovings, knitted goods, yarns, knitted fabrics, fabrics, etc.

The antimicrobially treated fibers of the invention may be used, for example, for the following:

Products made of the fibers described in the aforesaid may, e.g. be used to produce clothing (e.g. especially for the fields of sports, medicine, hospitals, laboratories, food production, food processing, food packaging and feeds, caring for people requiring care and sick individuals).

Products made of the fibers described in the aforesaid may, e.g. be used to produce filters, i.e. water filters (for use in hospitals, outdoor applications, emergency medical services, disaster relief operations, normal water supply in areas of poor drinking water quality, etc.), air filters (for use in air-conditioning systems, ventilation systems, mobile air conditioners, automobiles, in other transportation systems (ships, trains of all types, airplanes, etc.), in building ventilation systems, in halls and the ventilation systems of refrigerated warehouses in the food sector), filters for cooling lubricants as well as in a wide variety of additional applications.

Moreover, e.g. nonwovens, rovings, knitted fabrics and knitted goods, in order to produce absorbent materials, e.g. for use in food packagings (meat, fruit, sausages, vegetables, etc.) in the sanitary sector (incontinence pads and toppers, sanitary napkins and diapers), as absorbers, e.g. of blood or bodily fluids, used, e.g. in medical care, hospitals, dentistry, veterinary medicine, old-age homes, kindergartens and home care, as pads for wound treatment (e.g. in band-aids, bandages and dressings). Yarns may further be used for medical purposes, for example when suturing wounds.

The antimicrobially treated sheets according to the invention may, for example, be used in furniture, refrigerated warehouses, slaughterhouses, air-conditioning systems, electrically conductive surface coatings and ship hulls (anti-fouling).

The following examples serve to illustrate the invention:

Example 1 (Homopolymer)

The polymerization equipment consisted of a 500 ml 3-neck round bottom flask, an intensive cooler, a magnetic stirring plate, an inert gas flushing system, and a silicon oil bath controlled via the pistons' internal temperature.

27.60 g of tert-butylaminomethylstyrene (meta/para isomer mixture prepared from vinylbenzene chloride from Dow) and 40 ml of ethanol were placed in a 500 ml 3-neck flask. Thereafter, 0.185 g of azo-bis-(isobutyl nitrile) was dissolved in 5 ml of methyl ethyl ketone and added to the flask. This was followed by rinsing with nitrogen under rigorous stirring for 30 min, after which the flask was immersed in an oil bath with a temperature of 55° C. Under moderate stirring and a weak, continuous flow of nitrogen, after 5 h, the temperature was increased to 60° C. and the flask remained in the oil bath for another 22.5 h. The reaction solution obtained from the polymerization batch was placed in a 1 liter beaker, and the solution was kept in motion with a mechanical stirrer or a magnetic stirrer. Under rigorous stirring, 200 ml of water was added in droplets, causing the polymer to precipitate from the solution. The polymer was filtered and added back under heating and continuous stirring in ethanol. In turn, 150 ml of water were added to the solution in droplets, causing the polymer to precipitate and be separated out. This step was repeated 3 times in order to cleanse the polymer of residual monomer completely.

Thereafter, the polymer was dried for 5 hours at 100° C. in a vacuum drying cabinet (p<20 mbar). The polymer was characterized by determining its glass temperature via DSC and by determining its antimicrobial effectiveness.

The extraction steps and the drying of the polymer are necessary in order to remove residual monomer, low-molecular components and residual solvent from the polymer as completely as possible. Without this process, the glass temperatures determined via DSC may be up to 25° C. lower.

The polymer's glass temperature determined via DSC was 65° C. The log reduction after 24 hours amounted to 6.7 [innoculation germ content of 5.5 (log CFU/ml), reference germ content of 7.9 (log CFU/ml), residual germ content of 1.0 corresponds to NWG (log CFU/ml)].

Example 2 (Homopolymer)

27.60 g of tert-butylaminomethylstyrene (para isomer mixture prepared from 4-vinylbenzene chloride from TCl) and 40 ml of ethanol were placed in a 500 ml 3-neck flask. Thereafter, 0.185 g of azo-bis-(isobutyl nitrile) was dissolved in 5 ml of methyl ethyl ketone and added to the flask. The polymerization equipment was the same as in example 1. This was followed by rinsing with nitrogen under rigorous stirring for 30 min, after which the flask was immersed in an oil bath with a temperature of 55° C. Under moderate stirring and a weak, continuous flow of nitrogen, after 5 h, the temperature was increased to 60° C. and the flask remained in the oil bath for another 22.5 h. Thereafter, the polymerization batch was further processed and characterized as described in example 1.

The polymer's glass temperature determined via DSC was 90° C. The log reduction after 24 hours amounted to 6.9 [innoculation germ content of 5.5 (log CFU/ml), reference germ content of 7.9 (log CFU/ml), residual germ content of 1.0 corresponds to NWG (log CFU/ml)].

Example 3 (Homopolymer)

The polymerization equipment used was identical to that of the aforementioned examples.

28.90 g of (2-methylbutyl-2yl)aminomethylstyrene (para isomer mixture prepared from 4-vinylbenzene chloride from TCl) and 35 ml of ethanol were placed in a 500 ml 3-neck flask. Thereafter, 0.180 g of azo-bis-(isobutyl nitrile) was dissolved in 5 ml of methyl ethyl ketone and added to the flask. This was followed by rinsing with nitrogen under rigorous stirring for 40 min, after which the flask was immersed in an oil bath with a temperature of 55° C. Under moderate stirring and a weak, continuous flow of nitrogen, after 5 h, the temperature was increased to 60° C. and the flask remained in the oil bath for another 22.5 h. Thereafter, the polymerization batch was further processed and characterized as described in example 1. Thereafter, the polymer was dried for 4 hours at 100° C. in a vacuum drying cabinet (p<20 mbar). The polymer was characterized by determining its glass temperature via DSC and by determining its antimicrobial effectiveness.

The polymer's glass temperature determined via DSC was 75° C. The log reduction after 24 hours amounted to 7.0 [innoculation germ content of 6.8 (log CFU/ml), reference germ content of 7.9 (log CFU/ml), residual germ content of 1.0 corresponds to NWG (log CFU/ml)].

Example 4 (Copolymer)

13.80 g of tert-butylaminomethylstyrene (meta/para isomer mixture prepared from vinylbenzene chloride from Dow), 3.87 g of acrylonitrile and 40 ml of ethanol were placed in a 500 ml 3-neck flask. Thereafter, 0.185 g of azo-bis-(isobutyl nitrile) was dissolved in 5 ml methyl ethyl ketone and added to the flask. The polymerization equipment was the same as in example 1. This was followed by rinsing with nitrogen under rigorous stirring for 30 min, after which the flask was immersed in an oil bath with a temperature of 55° C. Under moderate stirring and a weak, continuous flow of nitrogen, after 5 h, the temperature was increased to 60° C. and the flask remained in the oil bath for another 22.5 h. Thereafter, the polymerization batch was further processed and characterized as described in example 1.

The polymer's glass temperature determined via DSC was 80° C. The log reduction after 24 hours amounted to 6.9 [innoculation germ content of 5.5 (log CFU/ml), reference germ content of 7.9 (log CFU/ml), residual germ content of 1.0 corresponds to NWG (log CFU/ml)].

Example 5 (Copolymer)

20.70 g of tert-butylaminomethylstyrene (para isomer mixture prepared from 4-vinylbenzene chloride from TCl), 7.34 g of methacrylonitrile and 60 ml of ethanol were placed in a 500 ml 3-neck flask. Thereafter, 0.278 g of azo-bis-(isobutyl nitrile) was dissolved in 7 ml of methyl ethyl ketone and added to the flask. The polymerization equipment was the same as in example 1. This was followed by rinsing with nitrogen under rigorous stirring for 30 min, after which the flask was immersed in an oil bath with a temperature of 55° C. Under moderate stirring and a weak, continuous flow of nitrogen, after 5 h, the temperature was increased to 60° C. and the flask remained in the oil bath for another 22.5 h. Thereafter, the polymerization batch was further processed and characterized as described in example 1.

The polymer's glass temperature determined via DSC was 85° C. The log reduction after 24 hours amounted to 6.7 [innoculation germ content of 5.5 (log CFU/ml), reference germ content of 7.9 (log CFU/ml), residual germ content of 1.0 corresponds to NWG (log CFU/ml)].

Example 6 (Copolymer)

21.70 g of (2-methylbutyl-2yl)aminomethylstyrene (para isomer mixture prepared from 4-vinylbenzene chloride from TCI), 7.36 g of methacrylonitrile and 60 ml ethanol were placed in a 500 ml 3-neck flask. Thereafter, 0.282 g of azo-bis-(isobutyl nitrile) was dissolved in 6 ml of methyl ethyl ketone and added to the flask. The polymerization equipment was the same as in example 1. This was followed by rinsing with nitrogen under rigorous stirring for 35 min, after which the flask was immersed in an oil bath with a temperature of 55° C. Under moderate stirring and a weak, continuous flow of nitrogen, after 5 h, the temperature was increased to 60° C. and the flask remained in the oil bath for another 22.5 h. Thereafter, the polymerization batch was further processed and characterized as described in example 1.

The polymer's glass temperature determined via DSC was 80° C. The log reduction after 24 hours amounted to 6.9 [innoculation germ content of 5.7 (log CFU/ml), reference germ content of 7.8 (log CFU/ml), residual germ content of 1.0 corresponds to NWG (log CFU/ml)].

Example 7 (Copolymer)

20.11 g of (2-methylbutyl-2yl)aminomethylstyrene (para isomer mixture prepared from 4-vinylbenzene chloride from TCI), 8.7 g of methacrylonitrile and 50 ml of ethanol were placed in a 500 ml 3-neck flask. Thereafter, 0.277 g of azo-bis-(isobutyl nitrile) was dissolved in 6 ml of methyl ethyl ketone and added to the flask. The polymerization equipment was the same as in example 1. This was followed by rinsing with nitrogen under rigorous stirring for 45 min, after which the flask was immersed in an oil bath with a temperature of 55° C. Under moderate stirring and a weak, continuous flow of nitrogen, after 5 h, the temperature was increased to 60° C. and the flask remained in the oil bath for another 24 h. Thereafter, the polymerization batch was further processed and characterized as described in example 1.

The polymer's glass temperature determined via DSC was 84° C. The log reduction after 24 hours amounted to 7.1 [innoculation germ content of 5.9 (log CFU/ml), reference germ content of 7.9 (log CFU/ml), residual germ content of 1.0 corresponds to NWG (log CFU/ml)].

Example 8 (Terpolymer)

17.14 g of tert-butylaminomethylstyrene (meta/para isomer mixture prepared from vinylbenzene chloride from Dow), 6.07 g of methacrylonitrile, 2.33 g of 4-vinylbenzoic acid, and 55 ml of ethanol were placed in a 500 ml 3-neck flask. Thereafter, 0.25 g of azo-bis-(isobutyl nitrile) was dissolved in 7 ml of methyl ethyl ketone and added to the flask. The polymerization equipment was the same as in example 1. This was followed by rinsing with nitrogen under rigorous stirring for 30 min, after which the flask was immersed in an oil bath with a temperature of 55° C. Under moderate stirring and a weak, continuous flow of nitrogen, after 5 h, the temperature was increased to 60° C. and the flask remained in the oil bath for another 22.5 h. Thereafter, the polymerization batch was further processed as described in example 1. Thereafter, the polymer was dried for 4 hours at 120° C. in a vacuum drying cabinet (p<20 mbar). Characterization was performed analogously to example 1.

The polymer's glass temperature determined via DSC was 115° C. The log reduction after 24 hours amounted to 6.5 [innoculation germ content of 5.6 (log CFU/ml), reference germ content of 7.5 (log CFU/ml), residual germ content of 1.0 corresponds to NWG (log CFU/ml)].

Example 9 (Terpolymer)

17.14 g of tert-butylaminomethylstyrene (para isomer mixture prepared from 4-vinylbenzene chloride from TCI), 9.52 g of 4-vinylpyridine, 1.36 g of methacrylonitrile, and 55 ml of ethanol were placed in a 500 ml 3-neck flask. Thereafter, 0.25 g of azo-bis-(isobutyl nitrile) was dissolved in 7 ml of methyl ethyl ketone and added to the flask. The polymerization equipment was the same as in example 1. This was followed by rinsing with nitrogen under rigorous stirring for 30 min, after which the flask was immersed in an oil bath with a temperature of 55° C. Under moderate stirring and a weak, continuous flow of nitrogen, after 5 h, the temperature was increased to 60° C. and the flask remained in the oil bath for another 22.5 h. Thereafter, the polymerization batch was further processed as described in example 1. Thereafter, the polymer was dried for 3 hours at 130° C. in a vacuum drying cabinet (p<20 mbar). Characterization was performed analogously to example 1.

The polymer's glass temperature determined via DSC was 120° C. The log reduction after 24 hours amounted to 6.5 [innoculation germ content of 5.6 (log CFU/ml), reference germ content of 7.5 (log CFU/ml), residual germ content of 1.0 corresponds to NWG (log CFU/ml)].

Example 10 (Terpolymer)

19.22 g of (2-methylbutyl-2yl)aminomethylstyrene (para isomer mixture prepared from 4-vinylbenzene chloride from TCI), 10.02 g of 4-vinylpyridine, 1.41 g of methacrylic acid, and 50 ml of ethanol were placed in a 500 ml 3-neck flask. Thereafter, 0.27 g of azo-bis-(isobutyl nitrile) was dissolved in 6 ml of methyl ethyl ketone and added to the flask. The polymerization equipment was the same as in example 1. This was followed by rinsing with nitrogen under rigorous stirring for 45 min, after which the flask was immersed in an oil bath with a temperature of 55° C. Under moderate stirring and a weak, continuous flow of nitrogen, after 5 h, the temperature was increased to 60° C. and the flask remained in the oil bath for another 22.5 h. Thereafter, the polymerization batch was further processed as described in example 1. Thereafter, the polymer was dried for 4 hours at 110° C. in a vacuum drying cabinet (p<20 mbar). Characterization was performed analogously to example 1.

The polymer's glass temperature determined via DSC was 104° C. The log reduction after 24 hours amounted to 7.1 [inoculation germ content of 5.8 (log CFU/ml), reference germ content of 7.9 (log CFU/ml), residual germ content of 1.0 corresponds to NWG (log CFU/ml)].

Example 11: Preparation of Antimicrobial Polymer Blends

The following antimicrobial polymers were used in the preparation:

(1) the homopolymer obtained from tert-butylaminomethylstyrene according to the invention was used: "TBAMS"

(2) Copolymers with a molar mixing ratio of the two monomers "TBAMS" and "AN" (acrylonitrile) of 1:0.1 and 1:0.2 and 1:0.3 were used: "TBAMS-AN-01," "TBAMS-AN-02" and "TBAMS-AN-03".

(3) A terpolymer based on tert-butylaminomethylenestyrene "TBAMS," vinylpyridine "VPy" and methacrylic acid "MAS" in a molar ratio of 1:0.3:0.05 were used: "TBAMS-VPy-03-MAS-005." In each case, tert-butylaminomethylstyrene was present as a meta/para isomer mixture.

(4) LDPE, PP, PS, ABS, aliphatic polyester TPU, aromatic polyester TPU and/or EVA were used as further thermoplastic polymers (=BLEPO).

Experiments Compounding in the Melt (CiM):

The polymer blends of experiments E1 to E19 were prepared from the antimicrobial polymers/copolymers according to the invention and further polymers in a Collin twin-screw extruder (Teachline model) with an output of 1.5 kg/h. The melt strand was cooled in a water bath and cut using a Collin granulator.

Experiments Mixing in Solution (MiS):

To prepare the polymer blends of experiments E20 to E26, an alkaline solution of the antimicrobial polymer/copolymer and the thermoplastic was prepared in a solvent in a stirrer tank. Thereafter, the solvent was removed in vacuum at a slightly higher temperature in an oil pump vacuum.

The polymer blend masses obtained were mechanically comminuted until they could be processed into molded parts using an injection molding machine. Using a laboratory injection molding machine (Babyplast 6/10P from Isoplast), circular molded articles with a thickness of 1.5 mm and a diameter of 40 mm (polymeric articles examined—PAE) were produced from the obtained polymer blends. Moreover, fibers were produced from the individual blends using an Amoco extruder "plasticizer" (settings: motor 5 A, 50 rpm, heating zone 1: 160° C., heating zones 2 to 3: 210° C., heating zone 4: 215° C., exhaust: 25 ft/min, 200 nozzles, diameter: 700 mm). In addition, CAST films were produced from the individual blends using an Amoco extruder "plasticizer" (settings: motor: 5 A, 50 rpm, heating zone 1 120° C., heating zones 2 to 4: 190° C., exhaust: 10 ft/min, air cooled over rollers).

The molded articles, films and fibers were examined to determine their antimicrobial effectiveness applying the test method described in the application. When reduced by 2 log steps compared to the initial germ content, the material is deemed antimicrobially effective. In the following table, antimicrobial effectiveness is characterized by "bacterial activity below the detection threshold (BDT) (no colony-forming units detectable) or by the number of log stage reductions.

| | Preparation of the polymer blend | BLEPO | Antimicrobial polymer of the invention | Part of antimicrobial polymer in % relative to the polymer blend mass | Mold | Antimicrobial effectiveness |
|---|---|---|---|---|---|---|
| E1 | CiM | LDPE | TBAMS | 5. | PAE | BDT |
| E2 | CiM | LDPE | TBAMS-AN-01 | 15 | PAE | BDT |
| E3 | CiM | LDPE | TBAMS-VPy-03 | 15 | PAE | 3 |
| E4 | CiM | LDPE | TBAMS | 15 | PAE | DT |
| E5 | CiM | LDPE | TBAMS | 15 | Fiber | BDT |
| E6 | CiM | LDPE | TBAMS | 10 | Film | BDT |
| E7 | CiM | LDPE | TBAMS-AN-01 | 20 | Fiber | BDT |
| E8 | CiM | PP | TBAMS | 30 | Fiber | 4 |
| E9 | CiM | PS | TBAMS | 20 | PAE | 4 |
| E10 | CiM | PS | TBAMS-AN-01 | 20 | PAE | BDT |
| E11 | CiM | ABS | TBAMS-VPy-03-MAS-005 | 25 | PAE | BDT |
| E12 | CiM | ABS | TBAMS | 15 | PAE | BDT |
| E13 | CiM | Aliph. TPU | TBAMS | 10 | PAE | BDT |
| E14 | CiM | Aliph. TPU | TBAMS-AN-03 | 25 | PAE | BDT |
| E15 | CiM | Arom. polyester TPU | TBAMS | 10 | PAE | BDT |
| E16 | CiM | Arom. polyester TPU | TBAMS-AN-02 | 15 | PAE | BDT |
| E17 | CiM | LLDPE | TBAMS | 10 | PAE | BDT |
| E17a | CiM | Arom. TPU polyether | TBAMS | 12 | PAE | BDT |
| E18 | CiM | EVA | TBAMS | 25 | PAE | BDT |
| E19 | CiM | EVA | TBAMS-VPy-03 | 25 | PAE | BDT |
| E20 | MiS | LDPE | TBAMS | 10 | PAE | 4 |
| E21 | MiS | LDPE | TBAMS | 15 | PAE | BDT |
| E22 | MiS | LDPE | TBAMS-AN-01 | 20 | PAE | 4 |
| E23 | MiS | Aliph. TPU (A1185) | TBAMS | 15 | PAE | 3 |
| E24 | MiS | Aliph. TPU (A1185) | TBAMS | 25 | PAE | BDT |
| E25 | MiS | Aliph. TPU (A1185) | TBAMS-AN-01 | 15 | PAE | 3 |
| E26 | MiS | Aliph. TPU (A1185) | TBAMS-AN-01 | 25 | PAE | BDT |

As evident from experiments E1 to E26, all of the polymer blends demonstrate an excellent antimicrobial effect.

Example 16: Printing on Films

Antimicrobial polymers according to the invention were dissolved in ethyl acetate (30% solution) and stirred into a UV-curing printing lacquer. UV curing was performed in ambient air and under exclusion of oxygen (using nitrogen) on a film printing machine applying the flexoprinting method.

Moreover, antimicrobial polymers according to the invention (30% solution in ethyl acetate) were worked into UV printing inks that were applied and cured applying the electron beam offset printing method.

The printed sides of the films were examined to determine their antimicrobial effectiveness applying the test method described in the application. When reduced by 2 log steps compared to the initial germ content, the material is deemed antimicrobially effective. In the following table, antimicrobial effectiveness is characterized by "bacterial activity below the detection threshold (BDT) (no colony-forming units detectable) or by the number of log stage reductions.

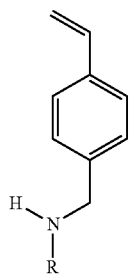

IIa

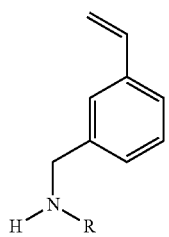

IIb

| | Printing method | Printed medium: Multilayer composite, top-most layer | Polymer of the invention added; 30% solution in ethyl acetate Mixture with lacquer at the ratio | Mold | Antimicrobial effectiveness |
|---|---|---|---|---|---|
| E1D | Flexoprinting | Corona-activated LDPE | TBAMS (1:0.2) | Film | BDT |
| E2D | Flexoprinting | Corona-activated LDPE | TBAMS-AN-01 (1:0.3) | Film | BDT |
| E3D | Flexoprinting | Corona-activated LDPE | TBAMS-AN-03 (1:0.3) | Film | BDT |
| E4D | Flexoprinting | Corona-activated LDPE | TBAMS-AN-03 (1:0.5) | Film | BDT |
| E5D | Flexoprinting | MSA-grafted LDPE | TBAMS | Film | BDT |
| E6D | Flexoprinting | MSA-grafted LDPE | TBAMS-AN-02 (1:0.3) | Film | BDT |
| E7D | Flexoprinting | Corona-activated PP | TBAMS (1:0.7) | Film | BDT |
| E8D | Flexoprinting | Corona-activated PP | TBAMS-AN-02 (1:0.7) | Film | BDT |
| E9D | Electron beams Offset printing | Corona-activated LDPE | TBAMS | Film | BDT |
| E10D | Electron beams Offset printing | Corona-activated LDPE | TBAMS-AN-03 (1:0.3) | Film | BDT |
| E11D | Electron beams Offset printing | Corona-activated PP | TBAMS | Film | BDT |
| E12D | Electron beams Offset printing | Corona-activated PP | TBAMS-AN-02 (1:0.3) | Film | BDT |

As evident from experiments E1D to E12D, all of the films demonstrate an excellent antimicrobial effect.

The invention claimed is:
1. A composition consisting essentially of an antimicrobial polymer obtainable by polymerizing a monomer, whereby the monomer is represented by the structural formulas IIa to IIc or mixtures thereof,

-continued

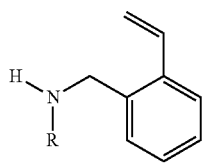

IIc wherein the residue R is ethyl, propyl, butyl, pentyl, hexyl and heptyl, cyclopropyl, cyclobutyl, cyclopentyl or cyclohexyl isopropyl, sec-butyl, iso-butyl, tert-butyl, 2-pentyl (sec. pentyl), 3-pentyl, 2-methyl-butyl, 3-methyl-butyl (isopentyl), 3-methyl-but-2-yl, 2-methylbut-2-yl, 2,2-dimethylpropyl (neopentyl), 2-methylpentyl, 3-methylpentyl, 2,3-dimethylbutyl, 2,2-dimethylbutyl (neohexyl) or 3-ethylpentyl, wherein the antimicrobial polymer's glass temperature is 60° C. to 200° C., and wherein the composition is a thermoplastic.

2. The composition according to claim 1, wherein the polymer is a homopolymer.

3. A composition comprising an antimicrobial copolymer obtainable by reacting at least one monomer of formulas IIa to IIc,

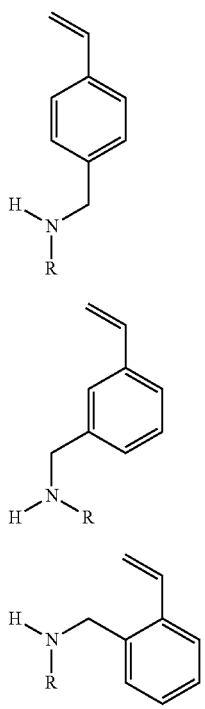

wherein the residue R is ethyl, propyl, butyl, pentyl, hexyl and heptyl, cyclopropyl, cyclobutyl, cyclopentyl or cyclohexyl isopropyl, sec-butyl, iso-butyl, tert-butyl, 2-pentyl (sec. pentyl), 3-pentyl, 2-methyl-butyl, 3-methyl-butyl (isopentyl), 3-methyl-but-2-yl, 2-methylbut-2-yl, 2,2-dimethylpropyl (neopentyl), 2-methylpentyl, 3-methylpentyl, 2,3-dimethylbutyl, 2,2-dimethylbutyl (neohexyl) or 3-ethylpentyl, with at least one further monomer, wherein the copolymer's glass temperature $T_G$ is 65° C. to 230° C., and wherein the composition is a thermoplastic.

4. The composition according to claim 3, wherein the further monomer is selected from the group consisting of (a) alkaline monomers, (b) acidic monomers, (c) associating monomers and (d) standard monomers, wherein the alkaline monomers (a) are selected from the group consisting of 1-vinylimidazole, 2-methyl-1-vinylimidazole, N-vinyloxazolidone, N-tert-butylaminoethyl methacrylate, N,N-dimethylaminoethyl methacrylate, N,N-diethylaminoethyl methacrylate, N,N-diisopropylaminoethyl methacrylate, 2-vinylpyridine, 3-vinylpyridine, 4-vinylpyridine, N-vinyltriazole, aminalkyl vinyl ether, and mixtures thereof, the acidic monomers (b) are selected from the group consisting of acrylic acid, chlorine acrylic acid, cyanoacrylic acid, methacrylic acid, itaconic acid and their anhydride, mesaconic acid, citraconic acid, crotonic acid, fumaric acid, maleic acid, vinylbenzoic acid and their isomers, cinnamic acid, stilbene dicarboxylic acid, vinylphosphonic acid, vinylbenzyl phosphonic acid, vinylbenzyl sulfonic acid, vinylsulfonic acid, 2-styrene sulfonic acid, 3-styrene sulfonic acid, 4-styrene sulfonic acid, 2-styrene phosphonic acid, 3-styrene phosphonic acid, 4-styrene phosphonic acid and mixtures thereof, the associating monomers (c) are selected from the group consisting of acrylonitrile, methacrylonitrile, N,N-dimethylacrylamide, N-ethacrylamide, N-tert-butylacrylamide, vinyl methylacetamide, N-tert-octylacrylamide, methyl cyanoacrylate, dicyanoethelyene, 1-nitrovinylene, 1-nitro- 1-methylvinylidene, vinylpyrrolidone, vinylcaprolactam, vinylbenzonitrile and mixtures thereof, and the standard monomers (d) are selected from the group consisting of ethylene, butadiene, isoprene, chloroprene, methacrylic ester, acrylic ester, vinyl ether, vinyl carbazole, vinyl thioether, vinyl ester, vinyl cyclohexene vinyl methyl chloride, vinylidene fluoride, vinyl acetate, vinyl silane, vinyl chloride, vinyl fluoride, vinylidene chloride, vinyl benzyl chloride, vinyl benzyl bromide, diesters of fumaric acid, diamides of fumaric acid, imides of maleic acid and mixtures thereof.

5. The antimicrobial copolymer according to claim 4, wherein the alkaline monomers (a) are present in a range of 0 to 95 mol %, the acidic monomers (b) are present in a range of 0 to 50 mol %, the associating monomers (c) are present in a range of 0 to 95 mol %, and the standard monomers (d) are present in a range of 0 to 70 mol %, relative to the total monomer content, wherein the number average molecular weight $M_n$ is 4,500 to 2,000,000 daltons, determined via gel permeation chromatography, and wherein the polymer's maximum water absorption is 35 wt. %, relative to the polymer's weight.

6. Method for preparing a composition according to claim 1, comprising the following steps:

(i) providing a monomer in accordance with formulas IIa to IIc, (ii) optionally, providing at least one additional monomer, and (iii) polymerizing the monomer or monomers by or without adding a polymerization initiator.

7. An antimicrobial polymer blend containing an antimicrobial polymer obtainable by polymerizing a monomer having a structure according to formula I

 (I), wherein

A is a radically polymerizable group of the formula —$CR^{V1}$=$CR^{V2}R^{V3}$, wherein $R^{V1}$, $R^{V2}$ and $R^{V3}$, independently of each other, are hydrogen, methyl, chloride, cyano or ester groups, B is an aromatic spacer, C' is an aliphatic spacer of the formula —CR$^{S1}$R$^{S2}$—,
wherein R$^{S1}$ and R$^{S2}$, independently of each other, are hydrogen or methyl, and D is an amine of the formula —NR$^{41}$R$^{42}$, wherein R$^{41}$ is a non-aromatic group with 2 to 7 carbon atoms, and R$^{42}$ is hydrogen, methyl or a non-aromatic group with 2 to 7 carbon atoms, wherein R$^{41}$ and R$^{42}$ are connected to each other and form a ring together with the nitrogen, wherein the ring includes 3 to 6 carbon atoms, wherein the ring formed can carry up to 4 methyl groups, wherein the polymer's glass temperature T$_G$ is 60° C. to 200° C., and/or a copolymer obtainable by reacting at least one monomer of the formula I, wherein groups A, B, C' and D are defined as set out above and at least one further monomer, wherein the copolymer's glass temperature T$_G$ is 65° C. to 230° C., and at least one blend polymer, and wherein the polymer blend is a thermoplastic.

8. The antimicrobial polymer blend according to claim 7, wherein the radically polymerizable group A is —CCN=CH$_2$, —CCH$_3$=CH$_2$, —CCl=CH$_2$, —CH=CH$_2$ or —C(COOCH$_3$)=CH$_2$ and/or the aromatic spacer B includes a phenylene, pyridyl, naphthylene or carbazol system and/or the non-aromatic spacer C' is —CH$_2$—, CHCH$_3$ or C(CH$_3$)$_2$ and the residue R$^{41}$ is—in group D—hydrogen or a branched aliphatic group with 3 to 7 carbon atoms and the residue R$^{42}$ is—in group D—a branched aliphatic group with 3 to 7 carbon atoms and/or R$^{41}$ and R$^{42}$ are connected to each other and, together with the nitrogen form a ring, wherein the ring contains 3 to 5 carbon atoms, wherein the ring formed can carry up to 4 methyl groups.

9. The antimicrobial polymer blend according to claim 7, wherein the monomer according to formula I is represented by the structural formulas IIa to IIc or mixtures thereof,

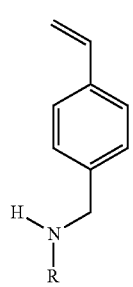

IIa

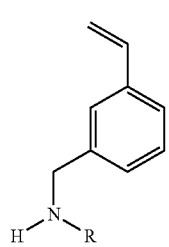

IIb

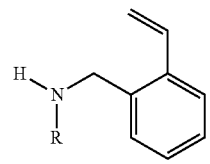

IIc and wherein the residue R is ethyl, propyl, butyl, pentyl, hexyl and heptyl, cyclopropyl, cyclobutyl, cyclopentyl or cyclohexyl isopropyl, sec-butyl, iso-butyl, tert-butyl, 2-pentyl (sec. pentyl), 3-pentyl, 2-methyl-butyl, 3-methyl-butyl (isopentyl), 3-methyl-but2-yl, 2-methylbut-2-yl, 2,2-dimethylpropyl (neopentyl), 2-methylpentyl, 3-methylpentyl, 2,3-dimethylbutyl, 2,2-dimethylbutyl (neohexyl) or 3-ethylpentyl.

10. The antimicrobial polymer blend according to claim 7, wherein the antimicrobial polymer is a homopolymer.

11. The antimicrobial polymer blend according to claim 7, comprising a copolymer obtainable by reacting at least one monomer according to formula I, wherein groups A, B, C' and D are defined as set out in claim 10 with at least one further monomer, wherein the copolymer's glass temperature T$_G$ is 65° C. to 230° C.

12. The antimicrobial polymer blend according to claim 11, wherein the further monomer is selected from the group consisting of (a) alkaline monomers, (b) acidic monomers, (c) associating monomers and (d) standard monomers, wherein the alkaline monomers (a) are selected from the group consisting of vinylimidazoles, N-vinyloxazolidone, N-tert-butylaminoethyl methacrylate, N,N-dimethylaminoethyl methacrylate, N,N-diethylaminoethyl methacrylate, N,N-diisopropylaminoethyl methacrylate, 2-vinylpyridine, 3-vinylpyridine, 4-vinylpyridine, N-vinyltriazole, aminalkyl vinyl ether, and mixtures thereof, the acidic monomers (b) are selected from the group consisting of acrylic acid, chlorine acrylic acid, cyanoacrylic acid, methacrylic acid, itaconic acid and their anhydride, mesaconic acid, citraconic acid, crotonic acid, fumaric acid, maleic acid, vinylbenzoic acid and their isomers, cinnamic acid, stilbene dicarboxylic acid, vinylphosphonic acid, vinylbenzyl phosphonic acid, vinylbenzyl sulfonic acid, vinylsulfonic acid, 2-styrene sulfonic acid, 3-styrene sulfonic acid, 4-styrene sulfonic acid, 2-styrene phosphonic acid, 3-styrene phosphonic acid, 4-styrene phosphonic acid and mixtures thereof, the associating monomers (c) are selected from the group consisting of acrylonitrile, methacrylonitrile, N,N-dimethylacrylamide, N-ethacrylamide, N-tert-butylacrylamide, vinyl methylacetamide, N-tert-octylacrylamide, methyl cyanoacrylate, dicyanoethelyene, 1-nitrovinylene, 1-nitro-1-methylvinylidene, vinylpyrrolidone, vinylcaprolactam, vinylbenzonitrile and mixtures thereof, and the standard monomers (d) are selected from the group consisting of ethylene, butadiene, isoprene, chloroprene, methacrylic ester, acrylic ester, vinyl ether, vinyl carbazole, vinyl thioether, vinyl ester, vinyl cyclohexene vinyl methyl chloride, vinylidene fluoride, vinyl acetate, vinyl silane, vinyl chloride, vinyl fluoride, vinylidene chloride, vinyl benzyl chloride, vinyl benzyl bromide, diesters of fumaric acid, diamides of fumaric acid, imides of maleic acid and mixtures thereof.

13. The antimicrobial polymer blend according to claim 12,
wherein the alkaline monomers (a) are present in a range of 0 to 95 mol %, the acidic monomers (b) are present in a range of 0 to 50 mol %, the associating monomers (c) are present in a range of 0 to 95 mol %, and the standard monomers (d) are present in a range of 0 to 70 mol %, relative to the total monomer content,
wherein the polymer blend's maximum water absorption is 35 wt. %, relative to the polymer blend's weight,
wherein the blend polymer is a thermoplastic, and
wherein the polymer blend can be molded at a temperature of 60 to 360° C. without decomposing and has a melt flow index of 0.01 to 70 g/10 min and a glass transition temperature of 60 to 200° C.

14. The antimicrobial polymer blend according to claim 7, wherein the blend polymer is selected from the group consisting of polyvinylpyridine and its copolymers, polyvinylpyrrolidine, polyvinylimidazoles, and their copolymers, polyvinylcarbazole and its copolymers, aromatic and aliphatic thermoplastic polyurethane (TPU), polypyrrole, polyacrylic acid (PAA), polymethacrylic acid (PMAA), polymethylmethacrylate (PMMA), MSA grafted polyethylene (MSA-PE), polychloroacrylic acid, and polycyanoacrylic acid, polyester, polybutylene therephthalate (PBT), polyethylene therephthalate (PET), polyamides (PA), polyarylamide, polyimide, polyacrylamides (PARA), polyamideimide (PAI), polyether block amides (PEBA), polyphthalamides (PPA), polyesteramide (PEA), polyoxymethylene (POM), polyetherketones, polyphenylene ether (PPE, PPO), polyamides, polycarbonates (PC), polyethersulfones, poly(2,6-diphenyl phenylene oxide), polyarylether (PAE), polyarylsulfones (PASU), polycyclohexylene dimethyleneterephthalate (PCT), polyethersulfones (PES), high-impact polystyrene (HIPS), polyolefines and their copolymers, ethylene propylene diene rubber (EPDM), polyoxymethylene (POM), polyvinylchlorides (PVC), polyvinylacetate (PVA), polyethylene vinylacetate (EVA), acrylonitrile styrene copolymer (SAN), acrylonitrile butadiene styrene (ABS), acrylic ester styrene acrylonitrile (ASA), acrylonitrile butadiene acrylate (ABA) and mixtures thereof.

15. The antimicrobial polymer blend according to claim 14, wherein the polyolefins are selected from the group consisting of linear low-density polyethylene (LLDPE), low-density polyethylene (LDPE), high-density polyethylene (HDPE) and polypropylene (PP).

16. A method for preparation of antimicrobial products, said method comprising processing the polymer blend according to claim 7 into molded parts using an injection molding machine or applying the polymer blend according to claim 10 to a substrate, wherein the polymer blend is a thermoplastic.

17. The method according to claim 16, wherein the preparation of antimicrobial products, is effected through thermoplastic processing of the polymer blend.

18. The method according to claim 17, wherein the preparation of antimicrobial products, is effected through application on substrates by printing, dipping, sintering, spraying, concealing, coating, laminating, gluing, fusing, fixing and/or lacquering.

19. Composite element containing
carrier material,
a composition according to claim 1 applied to said carrier material and optionally an adhesive promoter and/or adhesive.

20. Composite element according to claim 19, wherein this element is a composite film.

* * * * *